US010550384B2

(12) United States Patent
Church et al.

(10) Patent No.: US 10,550,384 B2
(45) Date of Patent: Feb. 4, 2020

(54) METHODS FOR SELECTING MICROBES FROM A DIVERSE GENETICALLY MODIFIED LIBRARY TO DETECT AND OPTIMIZE THE PRODUCTION OF METABOLITES

(71) Applicant: President and Fellows of Harvard College, Cambridge, MA (US)

(72) Inventors: George M. Church, Brookline, MA (US); Srivatsan Raman, Arlington, MA (US); Noah D. Taylor, Boston, MA (US); Jameson Rogers, Boston, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 396 days.

(21) Appl. No.: 14/775,025

(22) PCT Filed: Feb. 26, 2014

(86) PCT No.: PCT/US2014/018616
§ 371 (c)(1),
(2) Date: Sep. 11, 2015

(87) PCT Pub. No.: WO2014/158594
PCT Pub. Date: Oct. 2, 2014

(65) Prior Publication Data
US 2016/0017317 A1 Jan. 21, 2016

Related U.S. Application Data

(60) Provisional application No. 61/781,373, filed on Mar. 14, 2013.

(51) Int. Cl.
*C12N 15/10* (2006.01)
(52) U.S. Cl.
CPC .............................. *C12N 15/1058* (2013.01)
(58) Field of Classification Search
CPC ... C12N 15/1058; C12N 1/38; C12N 15/1034
See application file for complete search history.

(56) References Cited

U.S. PATENT DOCUMENTS

| | | | | |
|---|---|---|---|---|
| 6,555,672 B1* | 4/2003 | Liang | .................... | C07K 14/475 435/235.1 |
| 2007/0141574 A1* | 6/2007 | Keasling | ............ | C12N 15/1079 435/6.13 |
| 2009/0239243 A1* | 9/2009 | Engelhardt | ............ | A61K 31/00 435/7.8 |
| 2011/0003385 A1* | 1/2011 | Crabtree | .............. | C07D 498/18 435/375 |
| 2011/0177570 A1* | 7/2011 | Baart | .................... | C07K 14/245 435/145 |
| 2011/0207173 A1* | 8/2011 | Sodoyer | ................. | C12N 15/70 435/69.3 |
| 2011/0257041 A1* | 10/2011 | Babb | .................... | C12N 15/635 506/17 |
| 2012/0023619 A1* | 1/2012 | Samboju | .................. | B82Y 5/00 800/279 |
| 2012/0190089 A1* | 7/2012 | Buelter | ................ | C12N 9/0006 435/160 |
| 2012/0315682 A1* | 12/2012 | Dischert | .............. | C12N 9/0006 435/146 |
| 2013/0115658 A1* | 5/2013 | Szpirer | .................. | C12N 15/10 435/91.41 |
| 2013/0310458 A1* | 11/2013 | Eggeling | .............. | C12N 15/115 514/564 |

FOREIGN PATENT DOCUMENTS

| | | | |
|---|---|---|---|
| WO | 02/066657 A1 | 8/2002 | |
| WO | WO 2002/066657 A1 * | 8/2002 | ............. C12N 15/63 |

OTHER PUBLICATIONS

Temperton et al., Bias assessments of marine microbial biodiversity in fosmid libraries as evaluated by pyrosequencing, The ISME journal, Apr. 2, 2009, vol. 3, pp. 792-796. (Year: 2009).*
Carr et al., Enhanced multiplex genome engineering through co-operative oligonucleotide coselection, Nucleic Acids Research, May 25, 2012, vol. 40, No. 17, pp. 1-11. (Year: 2012).*
Kroll et al., Plasmid addiction systems; perspectives and applications in biotechnology. Microb Biotechnol, Nov. 2010, vol. 3, No. 6, pp. 634-657. (Year: 2010).*
Engelberg-Kulka et al in "mazEF: a chromosomal toxin-antitoxin module that triggers programmed cell death in bacteria" (Journal of Cell Science vol. 118, pp. 4327-4332). (Year: 2005).*
Van Sint Fiet et al (PNAS Feb. 2006 vol. 103, No. 6, pp. 1696-1698). (Year: 2006).*
Raman et al Evolution-guided optimization of biosynthetic pathways. (PNAS Dec. 1, 2014 vol. 111, No. 50, pp. 17803-17808). (Year: 2014).*
Temperton et al in "Bias in assessments of marine microbial biodiversity in fosmid libraries as evaluated by pyrosequencing" (The ISME Journal, Apr. 2, 2009, vol. 3, pp. 792-796). (Year: 2009).*
Carr et al in "Enhanced multiplex genome engineering through co-operative oligonucleotide co-selection" (Nucleic Acids Research, May 25, 2012, vol. 40, No. 17, pp. 1-11). (Year: 2012).*
International Search Report issued from corresponding PCT/US14/18616, dated Jul. 8, 2014.
Callura et al., Tracking, tuning, and terrilinating microbial physiology using synthetic riboregulators. Proc Natl Acad Sci USA, Sep. 7, 2010, vol. 107, No. 36, pp. 15898-15903.

(Continued)

*Primary Examiner* — Catherine S Hibbert
(74) *Attorney, Agent, or Firm* — Banner & Witcoff, Ltd.

(57) ABSTRACT

The present invention relates to genetically modified bacteria and methods of optimizing genetically modified bacteria for the production of a metabolite.

21 Claims, 8 Drawing Sheets
Specification includes a Sequence Listing.

(56) References Cited

OTHER PUBLICATIONS

Carr et al., Enhanced multiplex genome engineering through cooperative oligonucleotide coselection, Nucleic Acids Research, May 25, 2012, vol. 40, No. 17, pp. 1-11. Especially abstract; p. 1 0, col. 1, para 2.

Kroll et al., Plasmid addiction systems: perspectives and applications in biotechnology. Microb Biotechnol, Nov. 2010, vol. 3, No. 6, pp. 634-57. Entire document.

Temperton et al., Bias .iiJ. assessments of marine microbial biodiversity in fosrnid libraries as evaluated by pyrosequenCi) g. The ISME journal, Apr. 2, 2009, vol. 3, pp. 792-796. Especially abstract; p. 793, col. 1, para 1.

* cited by examiner

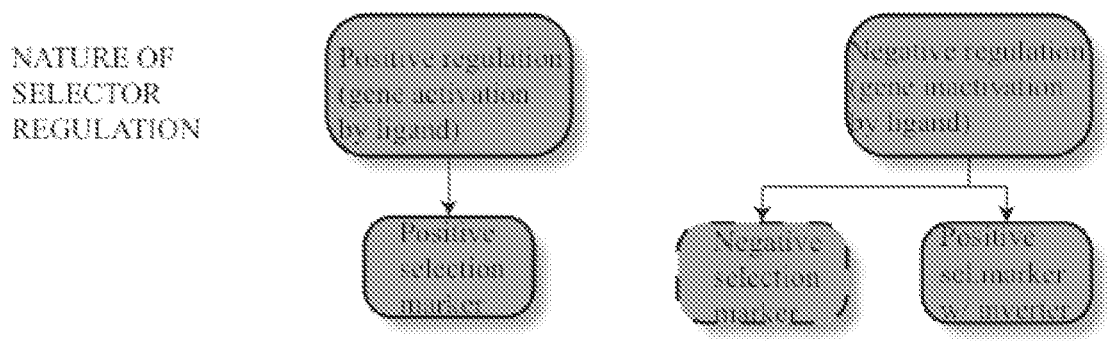
Figure 1
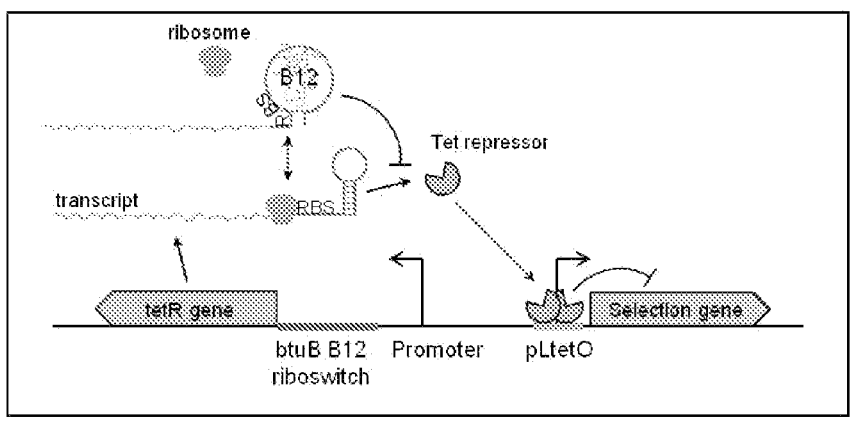
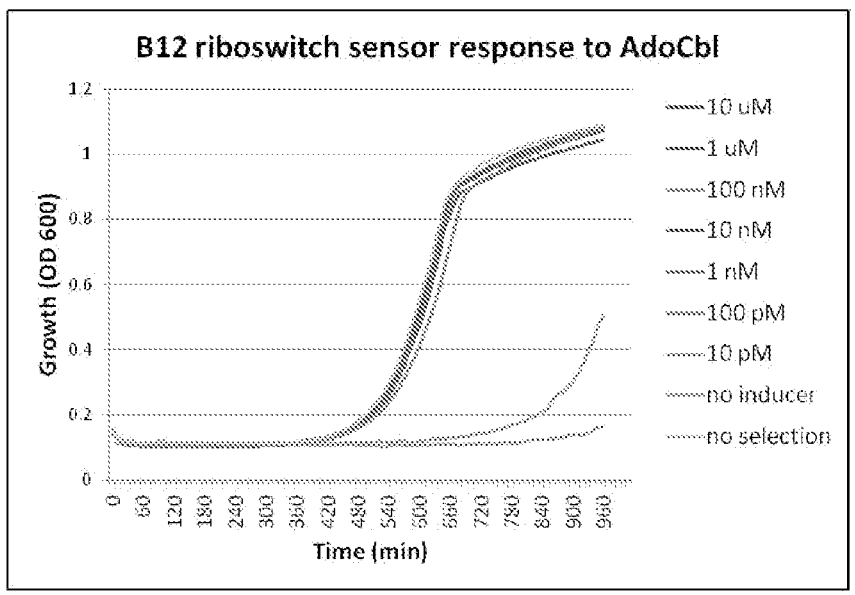
Figure 2A and 2B

SEQUENCE LISTING

```
<160> NUMBER OF SEQ ID NOS: 29

<210> SEQ ID NO 1
<211> LENGTH: 53
<212> TYPE: DNA
<213> ORGANISM: Artificial
<220> FEATURE:
<223> OTHER INFORMATION: PCR primer

<400> SEQUENCE: 1
aaaaaattta tttgcttttt atcccttgcg gcgatataat agattcatct tag            53

<210> SEQ ID NO 2
<211> LENGTH: 15
```

```
<212> TYPE: DNA
<213> ORGANISM: Artificial
<220> FEATURE:
<223> OTHER INFORMATION: PCR primer

<400> SEQUENCE: 2
aaagaggaga aatta                                                    15

<210> SEQ ID NO 3
<211> LENGTH: 69
<212> TYPE: DNA
<213> ORGANISM: Artificial
<220> FEATURE:
<223> OTHER INFORMATION: PCR primer

<400> SEQUENCE: 3
aattttacag tttgatcgcg ctaaatactg cttcaccaca aggaatgcaa tcgaacccca    60
gagtcccgc                                                           69

<210> SEQ ID NO 4
<211> LENGTH: 140
<212> TYPE: DNA
<213> ORGANISM: Artificial
<220> FEATURE:
<223> OTHER INFORMATION: PCR primer

<400> SEQUENCE: 4
ctgaacccag aaaggctcag gccgataaga atggggagca atttcttcat gaggatcctc    60
gggtcgctgg ctgaacccag aaaggctcag gccgataaga atggggagca atttcttcat   120
gaggatcctc gggtcgctgg                                              140

<210> SEQ ID NO 5
<211> LENGTH: 90
<212> TYPE: DNA
<213> ORGANISM: Artificial
<220> FEATURE:
<223> OTHER INFORMATION: PCR primer

<400> SEQUENCE: 5
ggcttctgct agaatccgca ataattttac agtttgatcg cgctaaatac tgcttcacca    60
caaggaatgc aatcgaaccc cagagtcccg                                    90

<210> SEQ ID NO 6
<211> LENGTH: 90
<212> TYPE: DNA
<213> ORGANISM: Artificial
<220> FEATURE:
<223> OTHER INFORMATION: PCR primer

<400> SEQUENCE: 6
ctggctcaac gaactgaacc cagaaaggct caggccgata agaatgggga gcaatttctt    60
cattgttgca ctcctgaaaa ttcgcgttag                                    90

<210> SEQ ID NO 7
<211> LENGTH: 84
<212> TYPE: DNA
<213> ORGANISM: Artificial
<220> FEATURE:
<223> OTHER INFORMATION: PCR primer

<400> SEQUENCE: 7
agccggataa gaagaggaaa cgcagcctaa ataatatctg gaataaagaa aaaaaattta    60
```

```
tttgcttttt atcccttgcg gcga                                              84
```

<210> SEQ ID NO 8
<211> LENGTH: 90
<212> TYPE: DNA
<213> ORGANISM: Artificial
<220> FEATURE:
<223> OTHER INFORMATION: PCR primer

<400> SEQUENCE: 8

```
cctcttcacc cttaatgtct ttgcaatctc ttaataaatt cagtgccatc cgcgcccggg      60
gagcccaagg gcacgccctg gcaccctgtt                                        90
```

<210> SEQ ID NO 9
<211> LENGTH: 109
<212> TYPE: DNA
<213> ORGANISM: Artificial
<220> FEATURE:
<223> OTHER INFORMATION: PCR primer

<400> SEQUENCE: 9

```
tccgcacgca ctaccaccag taacggtcat aacccttttcc gtaacaggcc tgcagcaaac     60
gacgaaaact acgctttagc agcttaatgt gtaggctgga gctgcttcg                 109
```

<210> SEQ ID NO 10
<211> LENGTH: 109
<212> TYPE: DNA
<213> ORGANISM: Artificial
<220> FEATURE:
<223> OTHER INFORMATION: PCR primer

<400> SEQUENCE: 10

```
tccgcacgca ctaccaccag taacggtcat aacccttttcc gtaacaggcc tgcagcaaac     60
gacgaaaact acgctgcagc agtttaatgt gtaggctgga gctgcttcg                 109
```

<210> SEQ ID NO 11
<211> LENGTH: 109
<212> TYPE: DNA
<213> ORGANISM: Artificial
<220> FEATURE:
<223> OTHER INFORMATION: PCR primer

<400> SEQUENCE: 11

```
tccgcacgca ctaccaccag taacggtcat aacccttttcc gtaacaggcc tgcagcaaac     60
gacgaaaact acgctttagt agcttaatgt gtaggctgga gctgcttcg                 109
```

<210> SEQ ID NO 12
<211> LENGTH: 109
<212> TYPE: DNA
<213> ORGANISM: Artificial
<220> FEATURE:
<223> OTHER INFORMATION: PCR primer

<400> SEQUENCE: 12

```
tccgcacgca ctaccaccag taacggtcat aacccttttcc gtaacaggcc tgcagcaaac     60
gacgaaaact acgctgcatc agtttaatgt gtaggctgga gctgcttcg                 109
```

<210> SEQ ID NO 13
<211> LENGTH: 82
<212> TYPE: DNA
<213> ORGANISM: Artificial
<220> FEATURE:
<223> OTHER INFORMATION: PCR primer

```
<400> SEQUENCE: 13
tacgttgcct tacgttcaga cggggccgaa gccccgtcgt cgtcaagttc ctattccgaa      60
gttcctattc tctagaaagt at                                              82

<210> SEQ ID NO 14
<211> LENGTH: 87
<212> TYPE: DNA
<213> ORGANISM: Artificial
<220> FEATURE:
<223> OTHER INFORMATION: PCR primer

<400> SEQUENCE: 14
cgggcgtatt ttttgagtta tcgagatttt caggagctaa ggaagctaaa ctgttataaa      60
aaaaggatca attttgaact ctctccc                                         87

<210> SEQ ID NO 15
<211> LENGTH: 71
<212> TYPE: DNA
<213> ORGANISM: Artificial
<220> FEATURE:
<223> OTHER INFORMATION: PCR primer

<400> SEQUENCE: 15
tgccattggg atatatcaac ggtggtatat ccagtgattt ttttctccat gaggatcctc      60
gggtcgctgg a                                                          71

<210> SEQ ID NO 16
<211> LENGTH: 85
<212> TYPE: DNA
<213> ORGANISM: Artificial
<220> FEATURE:
<223> OTHER INFORMATION: PCR primer

<400> SEQUENCE: 16
tgctagcaag taaggccgac taatacgact cactataggg agaagaagg aggtaactca       60 tagtgaaagt ggatgttggc ccgga                                           85

<210> SEQ ID NO 17
<211> LENGTH: 60
<212> TYPE: DNA
<213> ORGANISM: Artificial
<220> FEATURE:
<223> OTHER INFORMATION: PCR primer

<400> SEQUENCE: 17
taagaattca ttaaagagga gaaagaattc atgacagaag ataatattgc tccaatcacc      60

<210> SEQ ID NO 18
<211> LENGTH: 60
<212> TYPE: DNA
<213> ORGANISM: Artificial
<220> FEATURE:
<223> OTHER INFORMATION: PCR primer

<400> SEQUENCE: 18
atggtacctt tctcctcttt aatggtacct tacaacaatc tctcttcgaa tcttagttcg      60

<210> SEQ ID NO 19
<211> LENGTH: 24
<212> TYPE: DNA
<213> ORGANISM: Artificial
<220> FEATURE:
```

<223> OTHER INFORMATION: PCR primer

<400> SEQUENCE: 19
atgaaagtgg atgttggccc ggac                                      24

<210> SEQ ID NO 20
<211> LENGTH: 90
<212> TYPE: DNA
<213> ORGANISM: Artificial
<220> FEATURE:
<223> OTHER INFORMATION: PCR primer

<400> SEQUENCE: 20
ctttaacgga ggtgattgga gcaatattat cttctgtcat gaattcttyy byyyytttaa    60
tgaattctta ccacgacagg gtgcccggac                                    90

<210> SEQ ID NO 21
<211> LENGTH: 35
<212> TYPE: DNA
<213> ORGANISM: Artificial
<220> FEATURE:
<223> OTHER INFORMATION: PCR primer

<400> SEQUENCE: 21
aagaattcat gacagaagat aatattgctc caatc                          35

<210> SEQ ID NO 22
<211> LENGTH: 35
<212> TYPE: DNA
<213> ORGANISM: Artificial
<220> FEATURE:
<223> OTHER INFORMATION: PCR primer

<400> SEQUENCE: 22
tttaatggta ccttacaaca atctctcttc gaatc                          35

<210> SEQ ID NO 23
<211> LENGTH: 84
<212> TYPE: DNA
<213> ORGANISM: Artificial
<220> FEATURE:
<223> OTHER INFORMATION: PCR primer

<400> SEQUENCE: 23
aacgaaccag aacctgcagg aattccacac caggtctcaa gaattcatta aarrrrvrra    60
aggtaccatg aaagtggatg ttgg                                          84

<210> SEQ ID NO 24
<211> LENGTH: 85
<212> TYPE: DNA
<213> ORGANISM: Artificial
<220> FEATURE:
<223> OTHER INFORMATION: PCR primer

<400> SEQUENCE: 24
gcggttgttg aaggtatccg taaaccacac caggtctcag gtactttyyb yyyytttaat    60
ggtaccttac aacaatctct cttcg                                         85

<210> SEQ ID NO 25
<211> LENGTH: 25
<212> TYPE: DNA
<213> ORGANISM: Artificial
<220> FEATURE:
<223> OTHER INFORMATION: PCR primer

```
<400> SEQUENCE: 25
aacgaaccag aacctgcagg aattc                                        25

<210> SEQ ID NO 26
<211> LENGTH: 25
<212> TYPE: DNA
<213> ORGANISM: Artificial
<220> FEATURE:
<223> OTHER INFORMATION: PCR primer

<400> SEQUENCE: 26
gcggttgttg aaggtatccg taaac                                        25

<210> SEQ ID NO 27
<211> LENGTH: 38
<212> TYPE: DNA
<213> ORGANISM: Artificial
<220> FEATURE:
<223> OTHER INFORMATION: PCR primer

<400> SEQUENCE: 27
cacaccaggt ctcataccat gaaacggctt cttgttac                          38

<210> SEQ ID NO 28
<211> LENGTH: 44
<212> TYPE: DNA
<213> ORGANISM: Artificial
<220> FEATURE:
<223> OTHER INFORMATION: PCR primer

<400> SEQUENCE: 28
cacaccaggt ctcattctct ccctatagtg agtcgtatta gtcg                   44

<210> SEQ ID NO 29
<211> LENGTH: 11
<212> TYPE: PRT
<213> ORGANISM: Artificial
<220> FEATURE:
<223> OTHER INFORMATION: degenerate ribosome binding site

<400> SEQUENCE: 29

Asp Asp Arg Arg Arg Arg Arg Asp Asp Asp Asp
1               5                   10
```

METHODS FOR SELECTING MICROBES FROM A DIVERSE GENETICALLY MODIFIED LIBRARY TO DETECT AND OPTIMIZE THE PRODUCTION OF METABOLITES

RELATED APPLICATION DATA

This application is a National Stage Application under 35 U.S.C. 371 of co-pending PCT application number PCT/US2014/018616 designating the United States and filed Feb. 26, 2014; which claims the benefit of U.S. provisional application No. 61/781,373 and filed Mar. 14, 2013 each of which are hereby incorporated by reference in their entireties.

STATEMENT OF GOVERNMENT INTERESTS

This invention was made with government support under DE-FG02-02ER63445 awarded by the U.S. Department of Energy. The government has certain rights in the invention.

FIELD

The present invention relates in general to genetically modified bacteria and methods of optimizing genetically modified bacteria for the production of a metabolite.

BACKGROUND

Advances in genome engineering techniques of microbes have enabled facile, multiplexed modification of biosynthetic pathway genes to maximize production of high-value chemicals in the host organism. Selecting the successful strain among a large population of genotypes remains a major challenge. Accordingly, it is desirable to develop methods of identifying strains that are optimized for expression of exogenous DNA.

SUMMARY

Embodiments of the present disclosure are directed to methods of identifying a bacterial strain that is optimized for production of a metabolite from a population of bacterial strains. The methods described herein can be used to quickly identify the best strains for chemical production out of millions of less effective strains. Embodiments described herein are intended to be applicable to a broad range of chemicals that can be synthesized by microorganisms having their genomes genetically modified to include the synthetic pathway for a desired chemical.

According to one aspect, the genome of a microorganism is genetically modified to produce a recombinant microorganism by insertion into the microorganism's genome a DNA sequence, such as a synthetic DNA sequence, encoding a metabolite binding molecule (referred to herein as a "sensor"). According to one aspect, the sensor or metabolite binding molecule is an allosteric biomolecule that undergoes a conformation change upon binding a desired chemical or metabolite resulting in a change in gene regulation. Sensors and their corresponding binding partners are known to those of skill in the art and include allosteric molecules such as transcription factors (which bind to DNA to regulate expression of the bound DNA sequence), riboswitches, two-component signaling proteins and nuclear hormone receptors. The genome of the microorganism is also genetically modified to include DNA encoding for an antidote to a toxin. When expressed, the sensor regulates the production of the antidote within the microorganism. Depending on the nature of the sensor, it can regulate antidote production by repressing in the absence of the metabolite, activating in the presence of the metabolite, occluding ribosome binding site in the absence of metabolite etc. If the microorganism is placed into an environment of the toxin and no antidote or insufficient antidote is produced, the microorganism will die.

The microorganism has also been genetically modified to include DNA encoding genes to produce a metabolite binding partner of the sensor. Alternatively, endogenous genes in the microbe can produce the metabolite. The metabolite binding partner is a target chemical desired to be produced by the microorganism. The sensor which can be a DNA binding molecule will bind to the metabolite, when expressed. In this manner, the genetically modified microorganism can sense its own level of chemical production insofar as the sensor can sense for the presence within the microorganism of the metabolite. When the metabolite is produced by the cell, the metabolite binds to the sensor in a manner to regulate the antidote gene and, as a result, antidote is produced by the microorganism proportional to the amount of metabolite binding partner produced by the microorganism.

The microorganism is placed into an environment of a toxin counterpart to the antidote. In this manner, the antidote is referred to herein as a "selector" to the extent that antidote is produced by the cell in response to the level of metabolite present and in an amount sufficient to prevent the cell from dying. The level of antidote, which is proportional to the level of metabolite, selects strains for further modification and optimization. Microorganisms within a population of microorganisms that make more metabolite binding partner produce more antidote thereby promoting cell survivability. The concentration of toxin can be increased for a given strain to determine what level of toxin will result in cell death. In this manner, a strain can be selected for a given production of antidote, and accordingly, a given production of metabolite.

According to one aspect, a selected strain is subjected to genetic modification intended to optimize metabolite production by diversifying the population of microorganisms with a large number of semi-random chemical production designs, typically on the order of a billion. A genetically modified strain can be selected for its ability to produce antidote and therefore metabolite. A selected strain can be subjected to repeated rounds of genetic modification and selection in a toxin environment to produce a strain with optimized metabolite production. As toxin concentration is increased, only those genetically modified strains that produce sufficient metabolite, and therefore, antidote are able to survive. With each round of genetic modification and increased toxin concentration, a more robust metabolite producing strain is selected until the strain is optimized for metabolite production. Accordingly, an additional aspect includes identifying a strain that is optimized for production of the metabolite by identifying surviving strains subjected to increasing concentrations of toxin. A series of genetic selections query the level of antidote protein each microorganism is producing. Microorganisms are killed that have an antidote protein level insufficient to detoxify the microorganism. Microorganisms survive that have an antidote protein level sufficient to detoxify the microorganism.

According to one aspect, a method of selecting a subset of microorganisms for the production of a metabolite is provided which includes placing a population of microorganisms in an environment of a toxin, wherein the population of microorganisms has been genetically modified to include exogenous DNA encoding for an antidote to the toxin, wherein the population of microorganisms has been genetically modified to include exogenous DNA encoding a sensor which when expressed inhibits production of the antidote by the microorganisms, wherein the population of microorganisms has been genetically modified (may or may not be genetically modified) to include exogenous DNA encoding pathway genes to metabolite binding partner of the sensor or which may already include DNA encoding pathway genes to a metabolite binding partner, which when expressed binds to the DNA binding molecule to induce production of the antidote in a manner dependent on the concentration of the expressed metabolite, and selecting a subset of microorganisms that produce sufficient metabolite to prevent microbe death.

According to one aspect, the method further includes genetically modifying the subset of microorganisms to alter genes that produce the metabolite or to alter related metabolism, subjecting the subset of microorganisms to a subsequent environment of the toxin having a concentration greater than the environment, and selecting a subsequent subset of microorganisms the produce sufficient metabolite to prevent microorganism death.

According to one aspect, the method further comprises repeating in sequence (1) genetically modifying the subsequent subset of microorganisms by altering genes that produce the metabolite or by altering related metabolism, (2) subjecting the genetically altered microorganisms to a subsequent environment of a toxin having a concentration greater than a previous environment, and (3) selecting a further subsequent subset of microorganisms that produce sufficient metabolite to prevent microorganism death, said repeating step resulting in optimized metabolite producing microorganism.

According to one aspect, the sensor is a transcription factor, riboswitch, two-component signaling protein or a nuclear hormone receptor.

According to one aspect, the binding of the metabolite to the sensor activates gene expression to induce production of the antidote in a manner dependent on the concentration of the expressed metabolite.

According to one aspect, a positive selection marker is used as the antidote to select the subset of microorganisms that produce sufficient metabolite to prevent microorganism death.

According to one aspect, a dual selection marker is used to eliminate false positives and to select the subset of microorganisms that produce sufficient metabolite to prevent microorganism death.

According to one aspect, binding of the metabolite to the DNA binding protein represses gene expression to induce production of the antidote in a manner dependent on the concentration of the expressed metabolite.

According to one aspect, a negative selection marker is used to eliminate the subset of microorganisms that are false positives (i.e., detoxify despite not producing sufficient metabolite).

According to one aspect, the population of microorganisms have been genetically modified to include an additional exogenous DNA encoding the sensor which when expressed inhibits production of the antidote by the microorganisms.

According to one aspect, the microorganisms express a degradation tag to increase the degradation rate for antidote within the microorganisms to reduce false positives.

According to one aspect, translation of the sensor is attenuated to reduce false positives.

According to one aspect, the step of genetically modifying the subset of microorganisms to alter genes that produce the metabolite includes multiplexed automated genome engineering.

According to one aspect, the multiplexed automated genome engineering includes reducing spontaneous background mutants.

According to one aspect, the multiplexed automated genome engineering includes reducing spontaneous background mutants by pretreatment with a negative selector.

According to one aspect, the microorganisms have an escape rate of about 1 in 10 million.

According to one aspect, translation of the antidote is attenuated to reduce false positives.

According to one aspect, two or more distinct copies of the sensor biomolecule are expressed to reduce the rate of escape caused by genetic mutations that may inactivate a single copy of the sensor.

According to one aspect, the sensor biomolecule may regulate its own expression in addition to regulating the expression of the antidote.

According to one aspect, the sensor may regulate the expression of two or more distinct antidote proteins that confer survival in the presence of two or more distinct toxins.

According to one aspect, a method is providing for selecting a subset of microorganisms for the production of a metabolite which includes placing a population of microorganisms in an environment of a toxin, wherein the population of microorganisms have been genetically modified to include exogenous DNA encoding for an antidote to the toxin, wherein the population of microorganisms have been genetically modified to include exogenous DNA encoding a sensor which when expressed regulates production of the antidote by the microorganisms, wherein the population of microorganisms may or may not have been genetically modified to include pathway genes to produce a metabolite binding partner of the sensor, which when expressed binds to the sensor to induce production of the antidote in a manner dependent on the concentration of the expressed metabolite, repeatedly genetically modifying the microorganisms to alter genes that produce the metabolite, subjecting the microorganisms to negative selection, transforming surviving microorganisms with a plasmid including remaining exogenous DNA to complete the pathway to produce the metabolite, selecting microorganisms including the plasmid, and selecting a subset of microorganisms that produce sufficient metabolite to prevent microorganism death.

According to one aspect, a method is for reducing the false positives by negative selection after diversity generation by multiplex automated genome engineering or other methods, then subsequently transforming pathway complete gene(s) before applying positive selection.

BRIEF DESCRIPTION OF THE DRAWINGS

The foregoing and other features and advantages of the present invention will be more fully understood from the following detailed description of illustrative embodiments taken in conjunction with the accompanying drawing in which:

FIG. 1 is a schematic depicting selector options where the choice of selector depends of mode of gene regulation of sensor.

FIG. 2A depicts in schematic an inverter circuit illustrated with B12 riboswitch. FIG. 2B is a graph of a B12 response curve with inverter circuit.

DETAILED DESCRIPTION

Figure 3:
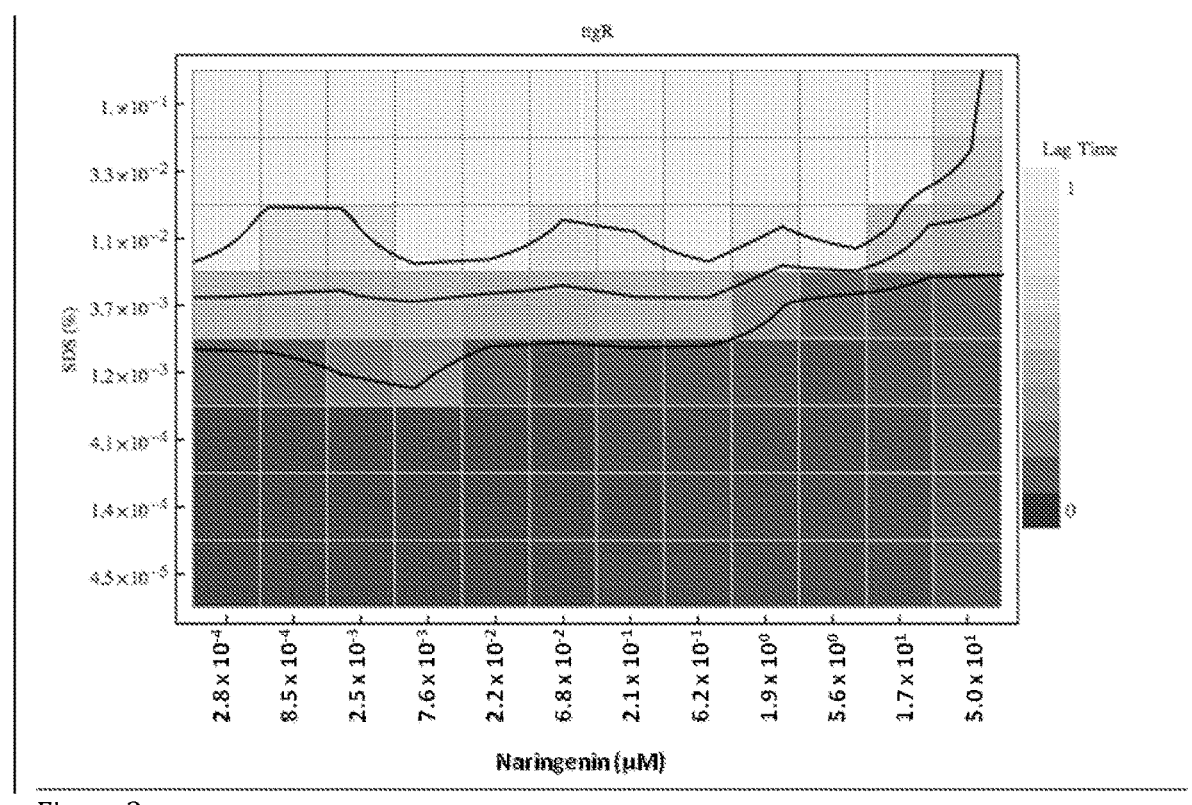
FIG. 3 is a dual gradient heat plot describing cell survivability as a function of metabolite concentration. Dark color is growth and light color is no growth. Naringenin sensed by TtgR against a toxin SDS concentration gradient.

Embodiments of the present disclosure include a recombinant host microorganism that includes one or more genetic modifications which program the microorganism to produce an exogenous sensor, a metabolite binding partner and an exogenous antidote to a toxin. When expressed the sensor regulates production of the antidote. When the pathway genes are expressed, the metabolite binding partner is produced which then binds to the sensor and promotes production of the antidote in proportion to the amount of metabolite.

Using this recombinant microorganism, a method is provided for selecting a recombinant strain that produces high amounts of the metabolite. The recombinant microorganism is placed into an environment of the toxin. If the recombinant microorganism produces sufficient antidote, which is proportional to the amount of metabolite produced, the strain survives and is selected as a suitable strain for the production of the metabolite. This selected strain can be subjected to repeated rounds of genetic modification (such as by using multiplexed automated genome engineering) designed to improve metabolite production and selection in response to a toxin level to create a recombinant strain optimized for metabolite production.

Standard recombinant DNA and molecular cloning techniques used herein are well known in the art and are described in Sambrook, J., Fritsch, E. F. and Maniatis, T., *Molecular Cloning: A Laboratory Manual*, $2^{nd}$ ed.; Cold Spring Harbor Laboratory: Cold Spring Harbor, N.Y., (1989) and by Silhavy, T. J., Bennan, M. L. and Enquist, L. W., *Experiments with Gene Fusions*; Cold Spring Harbor Laboratory: Cold Spring Harbor, N.Y., (1984); and by Ausubel, F. M. et. al., *Current Protocols in Molecular Biology*, Greene Publishing and Wiley-Interscience (1987) each of which are hereby incorporated by reference in their entireties.

Additional useful methods are described in manuals including Advanced Bacterial Genetics (Davis, Roth and Botstein, Cold Spring Harbor Laboratory, 1980), Experiments with Gene Fusions (Silhavy, Berman and Enquist, Cold Spring Harbor Laboratory, 1984), Experiments in Molecular Genetics (Miller, Cold Spring Harbor Laboratory, 1972) Experimental Techniques in Bacterial Genetics (Maloy, in Jones and Bartlett, 1990), and A Short Course in Bacterial Genetics (Miller, Cold Spring Harbor Laboratory 1992) each of which are hereby incorporated by reference in their entireties.

Microorganisms may be genetically modified to delete genes or incorporate genes by methods known to those of skill in the art. Vectors and plasmids useful for transformation of a variety of host cells are common and commercially available from companies such as Invitrogen Corp. (Carlsbad, Calif.), Stratagene (La Jolla, Calif.), New England Biolabs, Inc. (Beverly, Mass.) and Addgene (Cambridge, Mass.).

Typically, the vector or plasmid contains sequences directing transcription and translation of a relevant gene or genes, a selectable marker, and sequences allowing autonomous replication or chromosomal integration. Suitable vectors comprise a region 5' of the gene which harbors transcriptional initiation controls and a region 3' of the DNA fragment which controls transcription termination. Both control regions may be derived from genes homologous to the transformed host cell, although it is to be understood that such control regions may also be derived from genes that are not native to the species chosen as a production host.

Initiation control regions or promoters, which are useful to drive expression of the relevant pathway coding regions in the desired host cell are numerous and familiar to those skilled in the art. Virtually any promoter capable of driving these genetic elements is suitable for the present invention including, but not limited to, lac, ara, tet, trp, $IP_L$, $IP_R$, T7, tac, and trc (useful for expression in *Escherichia coli* and *Pseudomonas*); the amy, apr, npr promoters and various phage promoters useful for expression in *Bacillus subtilis*, and *Bacillus licheniformis*; nisA (useful for expression in Gram-positive bacteria, Eichenbaum et al. *Appl. Environ. Microbiol.* 64(8):2763-2769 (1998)); and the synthetic P11 promoter (useful for expression in *Lactobacillus plantarum*, Rud et al., *Microbiology* 152:1011-1019 (2006)). Termination control regions may also be derived from various genes native to the preferred hosts.

Certain vectors are capable of replicating in a broad range of host bacteria and can be transferred by conjugation. The complete and annotated sequence of pRK404 and three related vectors—pRK437, pRK442, and pRK442(H) are available. These derivatives have proven to be valuable tools for genetic manipulation in Gram-negative bacteria (Scott et al., Plasmid 50(1):74-79 (2003)). Several plasmid derivatives of broad-host-range Inc P4 plasmid RSF1010 are also available with promoters that can function in a range of Gram-negative bacteria. Plasmid pAYC36 and pAYC37, have active promoters along with multiple cloning sites to allow for the heterologous gene expression in Gram-negative bacteria.

Chromosomal gene replacement tools are also widely available. For example, a thermosensitive variant of the broad-host-range replicon pWV101 has been modified to construct a plasmid pVE6002 which can be used to create gene replacement in a range of Gram-positive bacteria (Maguin et al., J. Bacteriol. 174(17):5633-5638 (1992)). Additionally, in vitro transposomes are available to create random mutations in a variety of genomes from commercial sources such as EPICENTRE® (Madison, Wis.).

Vectors useful for the transformation of *E. coli* are common and commercially available. For example, the desired genes may be isolated from various sources, cloned onto a modified pUC19 vector and transformed into *E. coli* host cells. Alternatively, the genes encoding a desired biosynthetic pathway may be divided into multiple operons, cloned onto expression vectors, and transformed into various *E. coli* strains.

The *Lactobacillus* genus belongs to the Lactobacillales family and many plasmids and vectors used in the transformation of *Bacillus subtilis* and *Streptococcus* may be used for *Lactobacillus*. Non-limiting examples of suitable vectors include pAM.beta.1 and derivatives thereof (Renault et al., Gene 183:175-182 (1996); and O'Sullivan et al., Gene 137:227-231 (1993)); pMBB1 and pHW800, a derivative of pMBB1 (Wyckoff et al. Appl. Environ. Microbiol. 62:1481-1486 (1996)); pMG1, a conjugative plasmid (Tanimoto et al., J. Bacteriol. 184:5800-5804 (2002)); pNZ9520 (Kleerebezem et al., Appl. Environ. Microbiol. 63:4581-4584 (1997)); pAM401 (Fujimoto et al., Appl. Environ. Microbiol. 67:1262-1267 (2001)); and pAT392 (Arthur et al., Antimicrob. Agents Chemother. 38:1899-1903 (1994)). Several plasmids from *Lactobacillus plantarum* have also been reported (van Kranenburg R, Golic N, Bongers R, Leer R J, de Vos W M, Siezen R J, Kleerebezem M. Appl. Environ. Microbiol. 2005 March; 71(3): 1223-1230), which may be used for transformation.

Initiation control regions or promoters, which are useful to drive expression of the relevant pathway coding regions in the desired *Lactobacillus* host cell, may be obtained from *Lactobacillus* or other lactic acid bacteria, or other Gram-positive organisms. A non-limiting example is the nisA promoter from *Lactococcus*. Termination control regions may also be derived from various genes native to the preferred hosts or related bacteria.

The various genes for a desired biosynthetic or other desired pathway may be assembled into any suitable vector, such as those described above. The codons can be optimized for expression based on the codon index deduced from the genome sequences of the host strain, such as for *Lactobacillus plantarum* or *Lactobacillus arizonensis*. The plasmids may be introduced into the host cell using methods known in the art, such as electroporation, as described in any one of the following references: Cruz-Rodz et al. (Molecular Genetics and Genomics 224:1252-154 (1990)), Bringel and Hubert (Appl. Microbiol. Biotechnol. 33: 664-670 (1990)), and Teresa Alegre, Rodriguez and Mesas (FEMS Microbiology letters 241:73-77 (2004)). Plasmids can also be introduced to *Lactobacillus plantatrum* by conjugation (Shrago, Chassy and Dobrogosz Appl. Environ. Micro. 52: 574-576 (1986)). The desired biosynthetic pathway genes can also be integrated into the chromosome of *Lactobacillus* using integration vectors (Hols et al. Appl. Environ. Micro. 60:1401-1403 (1990); Jang et al. Micro. Lett. 24:191-195 (2003)).

Microorganisms which may serve as host cells and which may be genetically modified to produce recombinant microorganisms as described herein may include one or members of the genera *Clostridium, Escherichia, Rhodococcus, Pseudomonas, Bacillus, Lactobacillus Saccharomyces*, and *Enterococcus*. Particularly suitable microorganisms include *Escherichia coli, Bacillus subtilis, Saccharomyces cerevisiae*.

According to certain aspects, a microorganism is genetically modified to include one or more exogenous nucleic acids encoding for a sensor and its corresponding metabolite binding partner. Sensors are known to those of skill in the art and include transcription factors, riboswitches, two-component signaling proteins and nuclear hormone receptors. Exemplary sensor biomolecules, class type and their corresponding metabolite binding partners are listed in Table 1 below.

TABLE 1

| Sensor Gene | Molecule | Type of Sensor |
| --- | --- | --- |
| cdaR | glucaric acid | Transcriptional activator |
| ttgR | naringennin (flavanoids) | Transcriptional repressor |
| btuB riboswitch | cobalamin | Riboswitch |
| mphR | macrolides | Transcriptional repressor |
| tetR | tetracycline derivates | Transcriptional repressor |
| benM | muconic acid | Transcriptional activator |
| alkS | medium chain n-alkanes | Transcriptional activator |
| xylR | xylose | Transcriptional activator |
| araC | Arabinose | Transcriptional activator |
| gntR | Gluconate | Transcriptional repressor |
| galS | Galactose | Transcriptional repressor |
| trpR | tryptophan | Transcriptional repressor |
| qacR | Berberine | Transcriptional repressor |
| rmrR | Phytoalexin | Transcriptional repressor |
| cymR | Cumate | Transcriptional repressor |
| melR | Melibiose | Transcriptional activator |
| rafR | Raffinose | Transcriptional activator |
| nahR | Salicylate | Transcriptional activator |
| nocR | Nopaline | Transcriptional activator |
| clcR | Chlorobenzoate | Transcriptional activator |
| varR | Virginiamycin | Transcriptional repressor |
| rhaR | Rhamnose | Transcriptional repressor |
| PhoR | Phosphate | Two-component system |
| MalK | Malate | Two-component system |
| GlnK | Glutamine | Two-component system |
| Retinoic acid receptor | Retinoic acid | Nuclear hormone receptor |
| Estrogen receptor | Estrogen | Nuclear hormone receptor |
| Ecdysone receptor | Ecdysone | Nuclear hormone receptor |

It is to be understood that the examples of sensors and their corresponding metabolite binding partners are exemplary only and that one of skill in the art can readily identify additional sensors and their corresponding metabolite binding partners for use in the present disclosure. The transformed microorganism is intended to express the sensors and the metabolite under suitable conditions.

The biosynthetic pathways for production of any particular metabolite binding partner are known to those of skill in the art. The sensor sequence is identified based on published literature search. For example, biosynthetic pathways for the above metabolite binding partners and sensors are fully described in the following: cdaR (Monterrubio et al. 2000 J. Bacteriol 182(9):2672-4), tetR (Lutz and Bujard Nucleic Acids Res. 1997 25(6):1203-10), alkS (Canosa et al. Mol Micriobiol 2000 35(4):791-9), ttgR (Teran, et al. Antimicrob Agents Chemother. 47(10):3067-72 (2003)), btuB riboswitch (Nahvi, et al. Nucleic Acids Res. 32:143-150 (2004)); glucaric acid (Moon, et al. Appl Env Microbiol. 75:589-595 (2009)), naringenin (Santos, et al. Metabolic Engineering. 13:392-400 (2011)), alkanes (Steen, et al. 463:559-562 (2009)), cobalamin (Raux, et al. Cell Mol Life Sci. 57:1880-1893. (2000)), muconic acid (Niu, et al. Biotechnol Prog. 18:201-211. (2002)). Methods described herein can be used to insert the nucleic acids into the genome of the microorganism that are responsible for production of sensors and metabolite binding partners.

According to certain aspects, a microorganism is genetically modified to include one or more exogenous nucleic acids encoding an antidote to a toxin. Antidote and toxin pairs are known to those of skill in the art and include SDS:tolC, colicin:tolC (negative selection), kanamycin:kanamycin nucleotidyltransferase, chloramphenicol:chloramphenicol acyl tranferase, ampicillin:beta lactamase, tetracycline:tetracycline efflux pump tetA, nickel chloride: tetracycline efflux pump tetA (negative selection), 5-fluoroorotic acid:URA3 (negative selection). The transformed microorganism is intended to express the antidote under suitable conditions.

The genes for production of any particular antidote are known to those of skill in the art. For example, the genes for the above antidotes are fully described in tetA (Postle et al. Nucleic Acid Research 1984 12(12)4849-4863) tolC (Fralick J. Bacteriol 1996 178(19)5803-5805) Chloramphenicol acetyl transferase (Shaw et al. J Bacteriol. 1970 104(3): 1095-1105). Methods described herein can be used to insert the nucleic acids into the genome of the microorganism that are responsible for production of DNA binding molecules and metabolite binding partners.

According to one aspect, the transformed, recombinant microorganism expresses the sensor which regulates production of the antidote. When expressed, the sensor prevents the cell from expressing the antidote gene, either by blocking the expression (i.e. a repressor) or failing to activate the expression (i.e. activator) of the antidote unless the sensor is bound by the target metabolite, which leads to antidote expression by changing sensor function. Several regulation mechanisms are possible: for an allosteric transcription factor that is a repressor, the repressor protein blocks transcription of the antidote gene by binding a region of DNA 5' to the antidote gene unless the desired metabolite binds the repressor; for an allosteric transcription factor that is an activator, the activator recruits RNA polymerase to a region of DNA 5' to the antidote gene only when the desired metabolite binds to the activator; for an attenuating riboswitch, the riboswitch is encoded in the 5' untranslated region of a repressor regulating the transcription of the antidote gene, and attenuates translation of this repressor when bound to the target metabolite (See FIG. 2). According to a further aspect, the transformed, recombinant microorganism expresses the biosynthetic genes that produce the metabolite which binds to the sensor in a manner to promote production of the antidote. According to one aspect, the production of the antidote is proportional to the amount of metabolite binding partner that is produced by the microorganism and bound to sensor. In the absence of the metabolite, the sensor prevents production of antidote. Many individual sensor molecules re expressed in the cell. The binding of the metabolite to a sensor molecule is a reversible event, and switches that individual sensor molecule from a state in which it prevents antidote expression to a state in which it allows antidote expression. When the concentration of metabolite is low, the proportion of the sensor molecules bound to metabolite is low at any given time, hence the antidote is not expressed or expressed only slightly. As the concentration of metabolite increases, the proportion of sensor molecules bound to metabolite increases, which results in higher expression of antidote. This gives rise to dose-dependence of the antidote production and metabolite level. That is, the more metabolite binding partner that is produced by the cell, the higher the proportion of sensor molecules bound to metabolite molecules the cell to produce more antidote. The metabolite concentration below which there is no production of antidote is the detection threshold, and the metabolite concentration above which there is no further production of the antidote is the saturation point; these limits give rise to the dynamic range of the sensor-antidote system.

According to one aspect, a microorganism genetically modified as described herein to include exogenous nucleic acids which express a DNA binding molecule, a metabolite binding partner and an antidote to a toxin can be used to identify an optimum strain for production of the metabolite, since production of the antidote is proportional to production of the antidote. The recombinant microorganism is placed into a growth environment that includes a given concentration of toxin. If the microorganism does not produce enough antidote to counter the toxin, the microorganism will die. If the microorganism produces enough antidote to counter the toxin, the microorganism will live. The surviving microorganism is selected as a suitable producer of the metabolite. The selected microorganism strain can then be subjected to repeated rounds of multiplexed automated genome engineering targeted at genetic modifications intended to increase metabolite production by the microorganism. With each round, the genetically modified microorganism is subjected to increased levels of toxin and surviving strains are selected until a strain is identified having a desirable level of metabolite production. The strain can then be used to produce the metabolite, such as under large scale commercial settings.

An additional aspect of the present disclosure includes methods for lowering the escape rate of a population of recombinant microorganisms. That is, the number of genetically modified microorganisms that survive a toxin environment for reasons other than sufficient metabolite production to induce antidote production is lowered or reduced. This prevents the selection of surviving strains that do not produce increased levels of metabolite binding partners.

Example I

Building a Sensor-Selector Constructing and Inserting into *E. coli* Genome

To build a sensor-selector, a single copy of the nucleic acid(s) encoding the DNA binding molecule (sensor) is inserted into the *E coli* genome to minimize noise arising from copy number variability in plasmids. For a DNA binding molecule, its cognate promoter-operator regulates the antidote (selector), or alternatively a riboswitch is placed at the 5' end of the selector transcript.

The choice of the selector depends on the mode of gene regulation by the sensor. As shown in FIG. 1, in response to the metabolite, if the sensor activates gene expression (e.g., lacI or theophylline riboswitch), a positive selection marker is used, or if it represses gene expression (e.g., trpR or B12 riboswitch), a negative selection marker is used. To account for both modes of gene regulation, tolC gene, a dual selectable marker, is used as the main selector. Because negative selection of tolC is not nearly as titratable as positive selection, an inverter circuit as shown in FIG. 2 is provided such that the sensor indirectly activates a positive selection marker through an intermediate allosteric regulator. In FIG. 2, tetR, which is regulated by B12 riboswitch, is constitutively expressed to shut off the positive selector chloramphenicol acetyltransferase (CAT). When B12 metabolite is present, tetR is not translated, thus activating CAT expression.

TtgR sensor-selector construct: A linear DNA fragment (Sequence 4 appended at end) comprising a zeocin resistance gene cassette (the *Pseudomonas putida* strain KT2440 TtgR transcriptional regulator gene (Genbank Accession NP_743546.1) codon-optimized for expression in *E. coli* (Genscript, Piscataway, N.J.), a constitutive promoter apFAB101 (5'-AAAAAATTTATTTGCTTTTTATCCCTT-GCGGCGATATAATAGATTCATCTTAG), a RBS BB0034 (5'-AAAGAGGAGAAATTA) and the 257 basepairs of the *Pseudomonas putida* strain KT2440 genome 5' to the ttgA start codon was constructed by overlap PCR. This fragment was amplified by PCR with primers each appending 50 bp of homology to the MG1655 genome at the tolC gene locus (FWD: 5'-AATTTTACAGTTTGATCGCGCTAAATACT-GCTTCACCACAAGGAATGCAATCGAACCC CAGAGTCCCGC, REV: 5'-CTGAACCCA-GAAAGGCTCAGGCCGATAAGAATGGGGAG-CAATTTCTTCATGAGGATC CTCGGGTCGCTGGCT-GAACCCAGAAAGGCTCAGGCCGATAAGAATGGG GAGCAATTT CTTCATGAGGATC-CTCGGGTCGCTGG), and this PCR product was seamlessly integrated into the genome of ECNR2-T7 5' to the start codon of the tolC gene using lambda red recombination. The obtained strain was designated SSECttgR.

CdaR sensor-selector construct: A linear fragment of DNA (Sequence 1 Appended to end of this document) containing a beta lactamase expression cassette, the cdaR gene from *E. coli* MG1655, a promoter and RBS derived from pZE11 (Lutz and Bujard, Nucleic Acids Res. 1997 25(6):1203-10), and the 521 basepairs upstream of the *E. coli* MG1655 gudP start codon was constructed by Gibson assembly (Gibson, et al., Nature Meth. 6(5):343-345 (2009) and amplified with PCR primers that appended homology to the tolC loci of *E. coli* MG1655 (FW: 5-GGCTTCTGCTA-GAATCCGCAATAATTTTACAGTTT-GATCGCGCTAAATACTGCTTCAC CACAAGGAATG-CAATCGAACCCCAGAGTCCCG-3 RV: 5CTGGCTCAACGAACTGAACCCAGAAAGGCTCAG-GCCGATAAGAATGGGGAGCAATT TCTTCATTGTTG-CACTCCTGAAAATTCGCGTTAG-3). The linear fragment of DNA was then introduced 5' of the tolC start codon of *E. coli* strain ECNR2-T7 by lambda red recombineering such that the cloned gudP promoter region directed transcription of the tolC gene and the native transcriptional regulation of the tolC gene was abolished. The obtained strain was designated SSECcdaR.

Example II

*E. coli* Senses Desired Metabolites Using Sensor-Selector

The genetically modified *E. coli* with the sensor-selector modification is evaluated and quantified in terms microbe (microorganism) survivability. A dual gradient time course methodology is provided in which cells are subjected to increasing selection pressure and increasing metabolite concentration (exogenously provided). The dual gradient experiment is performed on a 96-well plate by mixing the metabolite to be sensed and toxin in different concentrations to create a gradient. The metabolite is serially diluted along the row (1-12) and toxin along the column (A-H). A time course experiment is then run to determine the cell density over time. The time course growth curves are fit using a four-parameter bacterial growth equation. By plotting time to half maximal growth, across different toxin and metabolite concentrations, a heat plot is generated.

Sensing naringenin: FIG. 3 shows a dual gradient heat map for the TtgR sensor-selector in *E. coli*. by sensing naringenin (metabolite). TtgR enables *E. coli* to survive the SDS (toxin) in a dose dependent manner. The x-axis is naringenin concentration from low to high (left to right) and y-axis is toxin concentration from low to high (bottom to top). As shown in FIG. 3, increasing toxin concentration requires increasing naringenin to ensure cell survival. In *E. coli* not containing TtgR sensor-selector, cells grow in presence of toxin with or without naringenin.

Example III

Determining Escape Rates of Sensor-Selectors

Figure 4:
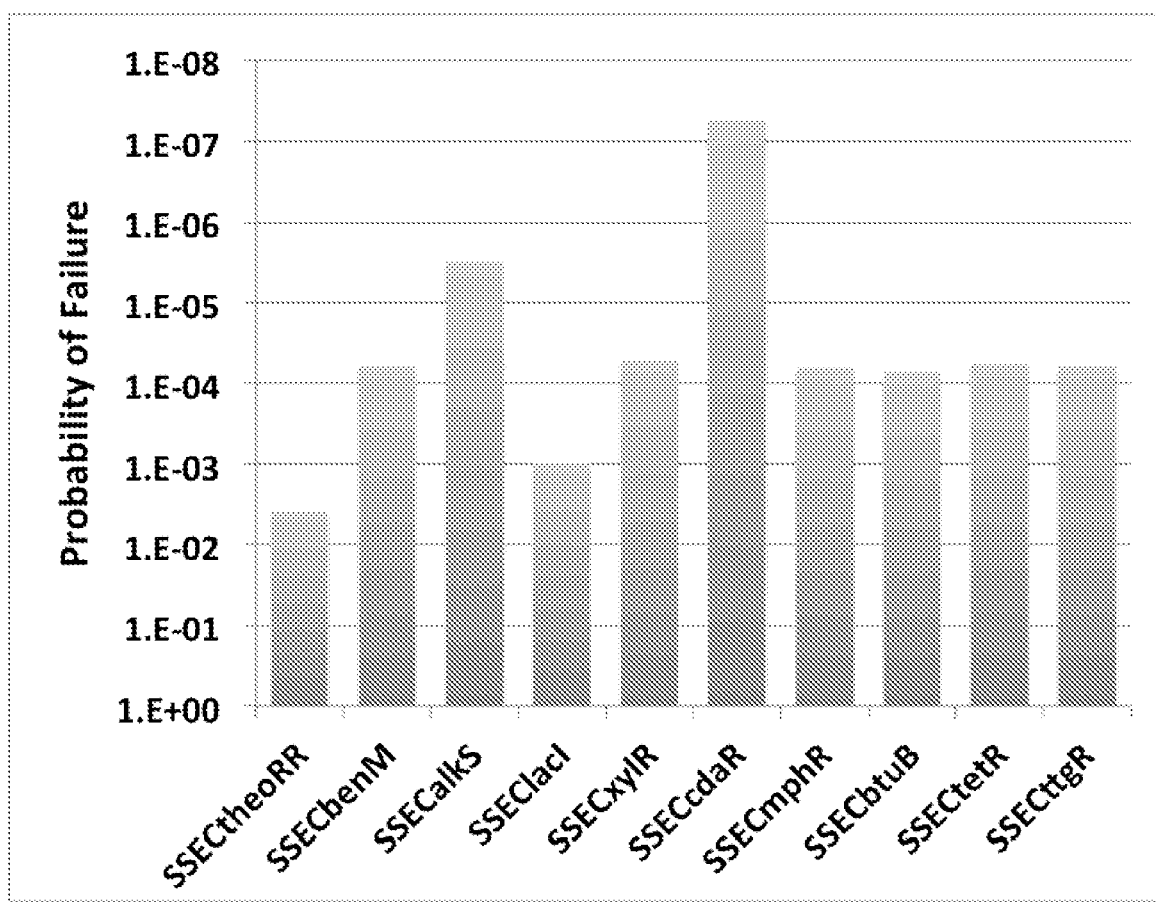
FIG. 4 is graph of probability of failure of 10 sensor-selector modules as a measure of the escape rate of sensor-selector strains.

Spurious activation of the selector (antidote) results in "escapees" that do not respond to the metabolite in a dose-dependent manner. These escapees are false positives that do not produce the metabolite at high levels but eventually take over the population by outcompeting the rest. Before deploying a sensor-selector to identify high producers, the false positive rate is determined. In order to determine the false positive rate, serial dilutions of SSECTtgR or SSECCdaR (or any other desired sensor) are plated on LB-Agar in the absence of the metabolite. The number of colony forming units is a measure of the escape rate. FIG. 4 shows the escape rates for the following sensor-selector strains: TtgR-tolC tetR-tolC, btuB riboswitch-CAT, mphR-tolC, cdaR-tolC, xylR-tolC, lacI-tolC, alkS-CAT, benM-tolC and theophylline riboswitch.

Example IV

Methods of Reducing Escape Rates

Figure 5:
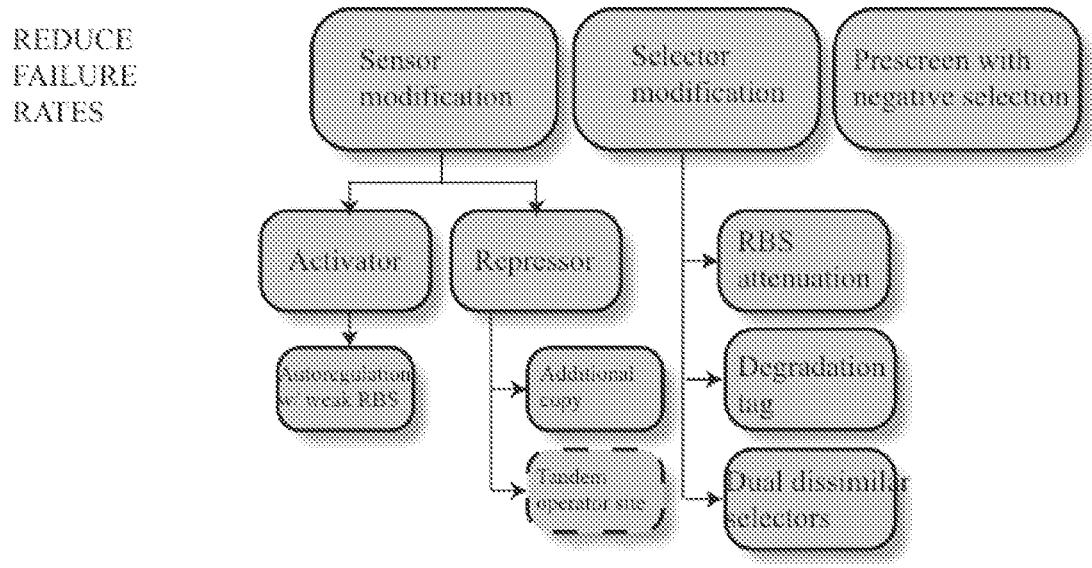
FIG. 5 is a schematic illustrating methods to reduce the failure rates of sensor-selectors.

FIG. 5 depicts in schematic methods to reduce failure rates (i.e. escape rates) in sensor-selectors. There are two major sensor-selector failure modes that causes escape— transcriptional leakage and spontaneous background mutants. Since transcription factors and riboswitches are not fully leak proof, basal expression of the selector causes selection bleed through. Transcriptional leakage can be addressed by changing the sensor or selector modules in the following ways. Sensors derived from transcriptional repressors need to be highly expressed to ensure that the equilibrium is strongly shifted towards a bound operator site. This is accomplished by introducing an additional copy of the sensor or by tandem operator site (demonstrated by Lutz and Bujard, Nucleic Acids Res. 1997 25(6):1203-10). With an additional copy of TtgR, the false positive rate drops by nearly four orders of magnitude.

Figure 7:
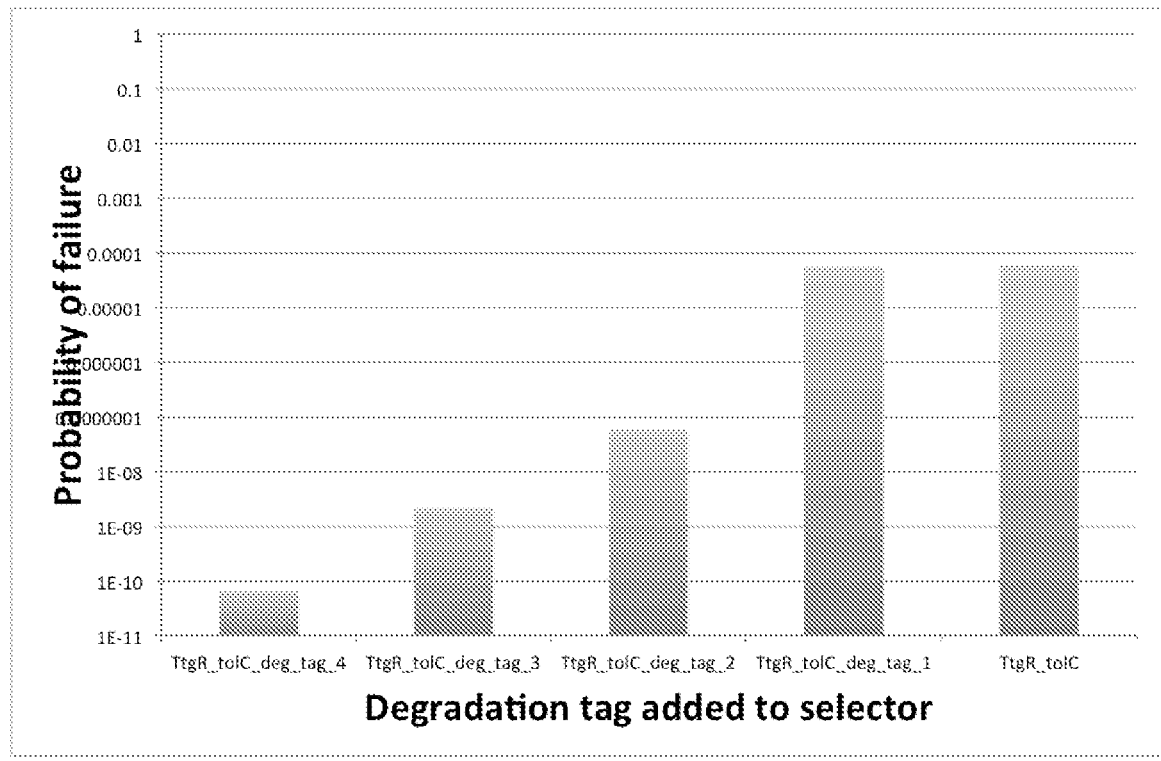
FIG. 7 is a graph illustrating that the addition of degradation tag to selector reduces false positive rate. The figure compares the probability of failure of TtgR_tolC with four degradation tag variants of different strengths.

However, in the case of transcriptional activators, overexpression is likely to lead to spurious selector activation. According to one aspect, feed-forward autoregulation of alkS, where sensor is expressed only in the presence of the metabolite, leads to reduction in false positives. Selector modifications center around two themes; one, reducing basal free selector proteins inside the cell, and two, having dual dissimilar selectors under the same sensor. Stochastic variation in free intracellular selector levels is likely to be sufficient to escape selection. Therefore, the selector levels are reduced by either appending a protein degradation tag to the selector or attenuating translation for changing spacing between Shine-Dalgarno site and translation start site. A key tradeoff is balancing reduction in false positive rate with a large operational range of the sensor. For instance, when the degradation tag is too strong, the sensor is insensitive to low metabolite concentration, even though false positives drop. FIG. 7 shows the inverse relationship between false positive rate and operational range by titration of three ssrA degradation tags of varying strengths.

Spontaneous background mutation, another cause for selection escape, occurs at higher rates in the mutator strain used for MAGE (multiplex automated genome engineering). Further, repeated cycles of MAGE causes dramatic increase in escape rate. However, several iterations of MAGE is required for targeting multiple alleles at reasonable efficiencies. Colicin pretreatment is performed that eliminates spontaneous background mutants after MAGE in a dosage dependent manner to restore escape rates at par with the starting strain.

Figure 6:
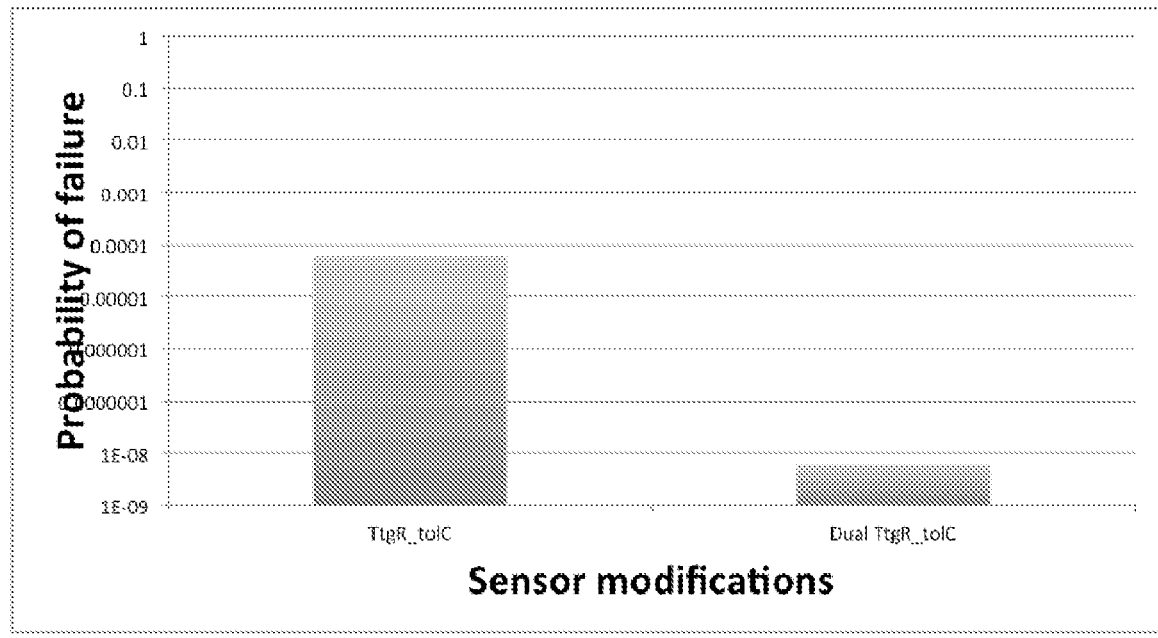
FIG. 6 is a graph comparing failure rates of TtgR_tolC and dual copy of TtgR with tolC. The failure rate drops by nearly four orders of magnitude.

Dual Sensor Module: Example: TtgR:

An additional copy of TtgR is inserted on the genome, creating a strain in which both ttgR genes must be mutated to prevent TtgR from repressing the selector in the absence of inducer. A linear DNA fragment comprising the promoter apFAB101, RBS BB0034 and codon-optimized ttgR gene from strain SSECttgR and a TetA tetracycline resistance gene cassette was constructed by overlap PCR. This fragment was PCR amplified with primers appending homology to the *E. coli* MG1655 genome locus 1529620 (FWD: 5'-AGCCGGATAAGAAGAGGAAACGCAGC-CTAAATAATATCTGGAATAAAGAAAAAAAA TTT-ATTTGCTTTTTATCCCTTGCGGCGA, REV: 5'-CCTCT-TCACCCTTAATGTCTTTGCAATCTCTTAATAAATT CAGTGCCATCCGCGCCCGG GGAGC-CCAAGGGCACGCCCTGGCACCCTGTT) and inserted into the genome of SSECttgR using lambda red recombination. This obtained strain was designated SSECttgR2. As shown in FIG. 6, additional copy of TtgR reduces failure rate by nearly four orders of magnitude.

Selector Degradation Tag: Example: TtgR Sensor-Selector with ssrA Tags:

By adding degradation tag, any free-floating antidote inside the cell is destabilized. The degradation tag is a short peptide that is appended to the end of the antidote protein that results in breakdown of any free-floating antidote. The strength of the degradation tag determines how quickly and efficiently the antidote protein can be degraded. A weak degradation tag may not completely destroy all free-floating antidote proteins, while a strong degradation tag may destroy the antidote protein expressed in response to the target metabolite causing even the high producers to perish. Therefore, it is important to tune the degradation tag strength. FIG. 7 shows the reduction in the failure rate with degradation tag titration.

The four degradation tags were added to the end of tolC using lambda-red recombineering using zeocin as the selection marker. The four degradation tag sequences are appended to tolC using following primer combinations:

```
tolC_deg_tag_4_zeo_F
TCCGCACGCACTACCACCAGTAACGGTCATAACCCTTTCCGTAACAGGCC

TGCAGCAAACGACGAAAACTACGCTTTAGCAGCTTAATGTGTAGGCTGGA

GCTGCTTCG tolC_deg_tag_3_zeo_F
TCCGCACGCACTACCACCAGTAACGGTCATAACCCTTTCCGTAACAGGCC

TGCAGCAAACGACGAAAACTACGCTGCAGCAGTTTAATGTGTAGGCTGGA

GCTGCTTCG tolC_deg_tag_2_zeo_F
TCCGCACGCACTACCACCAGTAACGGTCATAACCCTTTCCGTAACAGGCC

TGCAGCAAACGACGAAAACTACGCTTTAGTAGCTTAATGTGTAGGCTGGA

GCTGCTTCG tolC_deg_tag_1_zeo_F
TCCGCACGCACTACCACCAGTAACGGTCATAACCCTTTCCGTAACAGGCC

TGCAGCAAACGACGAAAACTACGCTGCATCAGTTTAATGTGTAGGCTGGA

GCTGCTTCG

Zeo_tolC_downstream_locus_R
TACGTTGCCTTACGTTCAGACGGGGCCGAAGCCCCGTCGTCGTCAAGTTC

CTATTCCGAAGTTCCTATTCTCTAGAAAGTAT
```

Selector RBS Attenuation: Example: TtgR Sensor-Selector with Modified Shine Dalgarno Sequences:

Titration of degradation tag strength can be difficult for some sensor-selectors because of large step changes in failure rates with different tags. For finer control, a method is provided to control antidote protein levels by tuning the ribosome binding site. The ribosome recognizes a key motif called Shine-Dalgarno sequence that is exactly 7-8 base pairs away from the translation start site. By varying the spacing and composition between the Shine Dalgarno sequence and translation start site, the ribosome binding affinity is tuned to the motif and hence antidote protein translation. By increasing or decreasing the spacing, the amount of spuriously translated protein can be tightly regulated to reduce false positives.

Dual Selectors: Example: TtgR with tolC and TtgR with CAT:

By placing the tolC and CAT genes under independent promoters controlled by the TtgR regulator, two distinct selection mechanisms are used and either one if active may kill the cell. A linear DNA fragment comprising a tetracycline resistance gene cassette and the 257 basepairs of the *Pseudomonas putida* strain KT2440 genome 5' to the ttgA start codon was constructed by overlap PCR. This fragment was amplified using PCR primers (FWD: 5'-CGGGCGT-ATTTTTTGAGTTATCGAGATTTTCAG-GAGCTAAGGAAGCTAAACTGTTATA AAAAAAGGATCAATTTTGAACTCTCTCCC, REV: 5'-TGCCATTGGGATATATCAACGGTGGTATATCCAGT-GATTTTTTCTCCATGAGGATCC TCGGGTCGCTGGA) appending homology to the *E. coli* strain EcNR2 genome directly 5' to the chloramphenicol acyltransferase (CAT) locus. This construct was integrated by lambda red recombination directly 5' to the CAT gene locus of strain SSECttgR. This dual selector strategy can be used in conjunction with two copies of the ttgR regulator gene.

Autoregulation with Feed Forward Loop: Example: AlkS:

To create an alkane-sensing strain, AlkS activator from *Pseudomonas oleovorans* and the promoter pAlkB whose transcription it controls, have been inserted 5' to tolC gene of EcNR2 (Wang et al. Nature 460, 894-898 2009). To use autoregulation in a feed-forward manner, pAlkB promoter is also used to control the transcription of the alkS gene. This keeps the expression of AlkS low until alkanes are sensed, increasing the expression of AlkS as well as its target selector, TolC, in a feed-forward manner which amplifies the signal and improves sensor-selector robustness.

Figure 8:
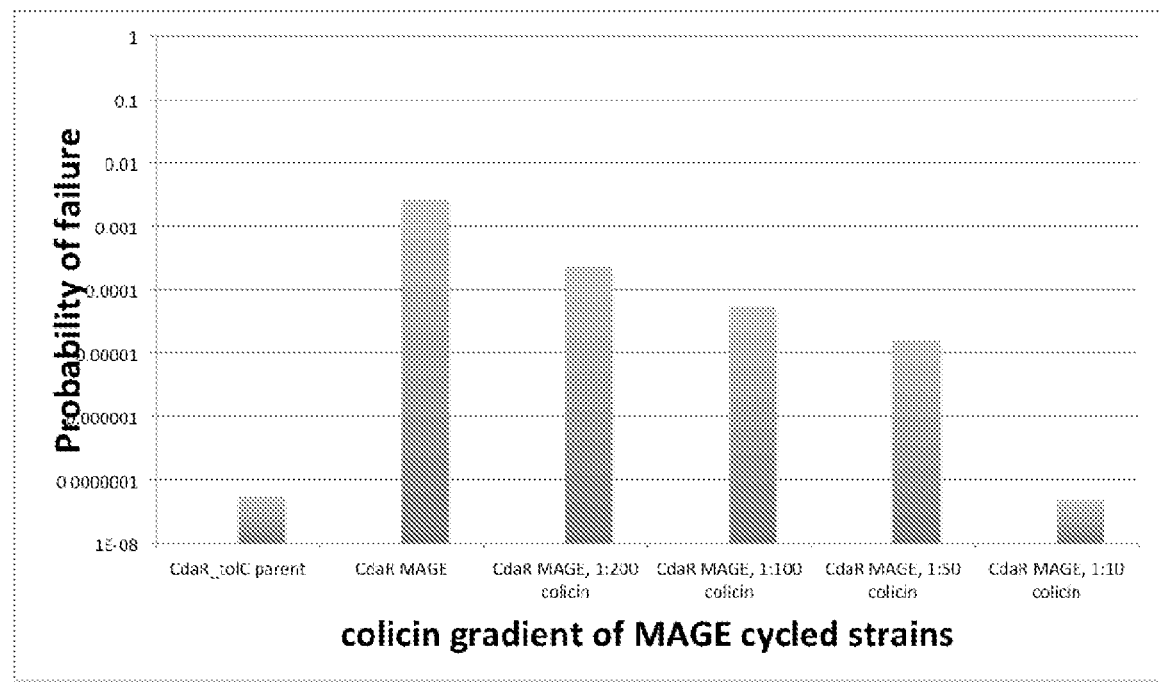
FIG. 8 is a graph illustrating the effect of prescreening with negative selection to eliminate false positives. The graph shows a comparison of failure of rate of glucaric acid pathway parent strain and the same strain after 5 cycles of MAGE and treated with different concentration of colicin.

Pre-Screening with Negative Selection: Example: Glucaric Acid Pathway Strain:

Probability of failure due to occurrence of spontaneous mutants increases with the number of MAGE cycles. In FIG. 8, after 5 cycles of MAGE in the glucaric acid pathway strain the failure rate increases by several orders of magnitude compared to the starting strain. By pretreatment with negative selection (protein colicin E1), false positives can be eliminated in a dose-dependent manner.

Example V

Determining Dynamic Range of Sensor by Dual Gradient Heat Plot

The dynamic range is the metabolite concentration range over which the sensor is operational. The sensor cannot detect concentrations below the lower threshold. Above the higher threshold, the sensor is saturated. The dynamic range can be evaluated with a dual gradient heat map. The upper threshold of the dynamic range denotes the maximum metabolite concentration that can be selected for from a population of diversified microbes.

Figure 9:
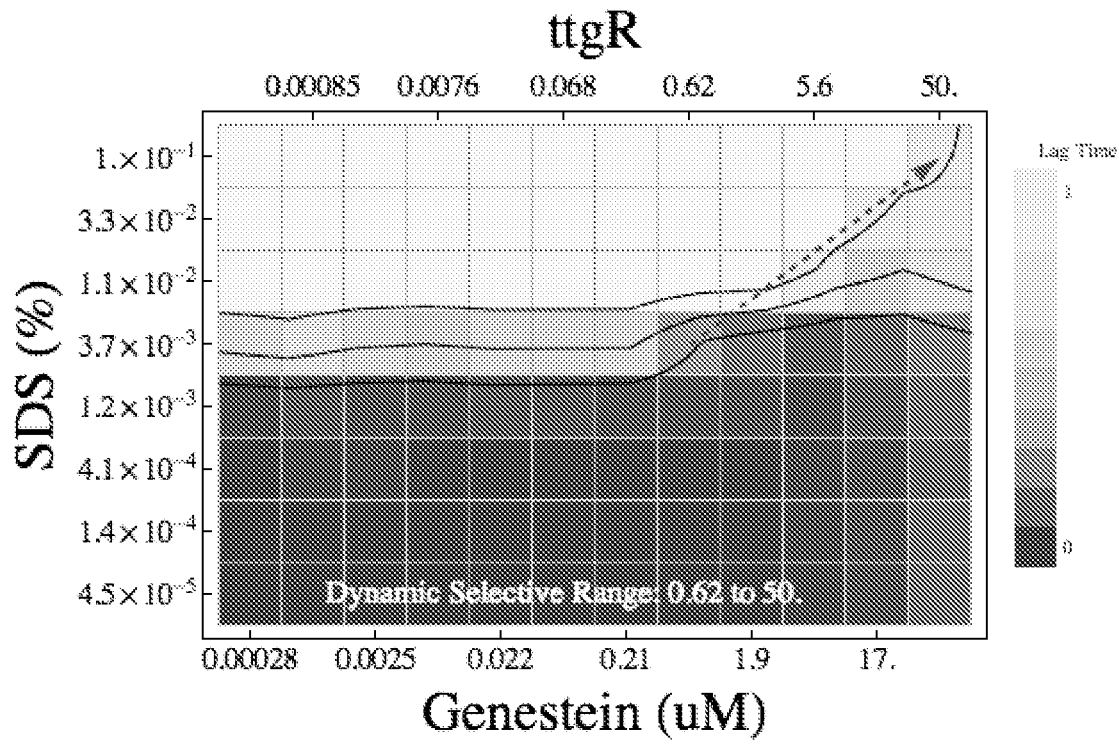
FIG. 9 is a graph of the dynamic range of TtgR. The arrow denotes the dynamic range of TtgR for metabolite genestein.

Example Heat Plot: TtgR:

A dual gradient heat map is generated using the method of Example 2. In FIG. 9, the arrow denotes the dynamic range of TtgR for the metabolite genestein.

Example Data for Other Sensors: TtgR, tetR, btuB Riboswitch, mphR, cdaR, xylR, lacI, alkS, benM and Theophylline Riboswitch

[Is there other data/heat maps to present for the above?]

Example VI

Methods for Modifying Sensor Dynamic Range

According to certain aspects, methods are provided to decrease the effective intracellular concentration of the sensed molecule by exporting, enzymatically degrading, or sequestering the ligand.

Figure 10:
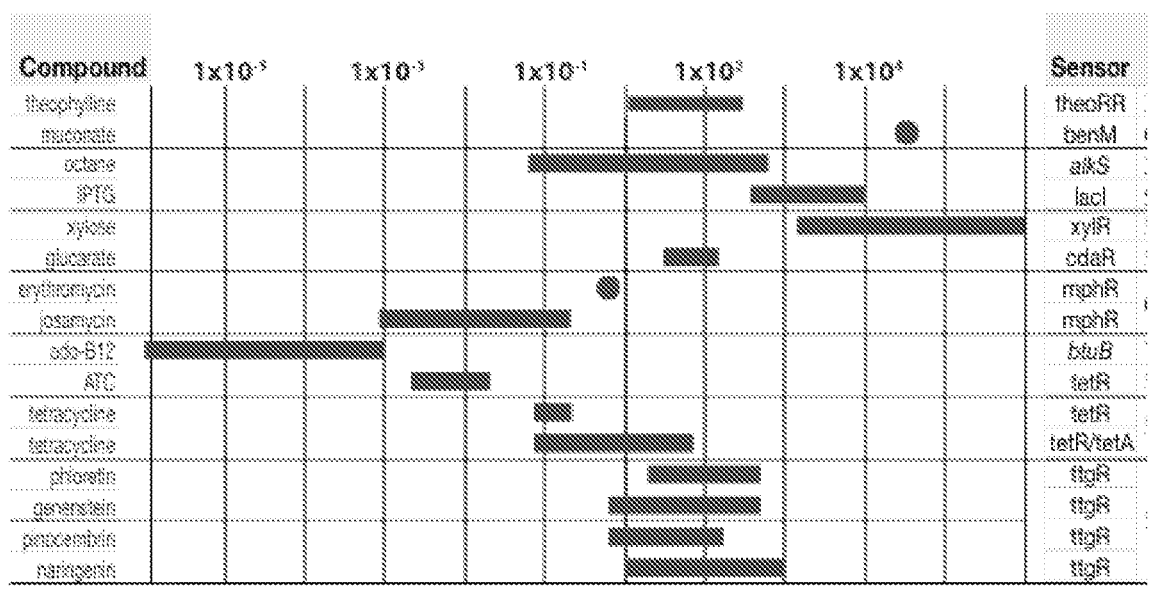
FIG. 10 is a graph of the dynamic range of ten sensor-selectors and their cognate metabolites.

Example Using an Exporter: Tetracycline and TetA Membrane Pump:

The TetR sensor-selector strain responds to the presence of sublethal concentrations of tetracycline (See FIG. 10). By including a copy of the tetA gene encoding the TetA tetracycline efflux pump protein, the intracellular concentration of tetracycline is reduced, alleviating toxicity and allowing the sensor-selector to confer a growth advantage on the strain to a higher concentration of tetracycline, expanding the dynamic range of the sensor-selector 4-fold by increasing the upper bound concentration (See FIG. 10).

Example Using Degradation Enzyme: Glucaric Acid and gudD Glucarate Dehydratase:

A catabolic enzyme is used to convert the sensed molecule into a form that does not activate the sensor response. *E. coli* enzyme GudD catalyzes the dehydration of D-glucaric acid to 5-keto-4-deoxy-D-glucarate (KDG; Gulick et al., Biochemistry 39(16):4590-4602 (2000)). By expressing a high level of this enzyme in the CdaR sensor-selector strain, the response to glucaric acid can be reduced by converting some of the glucaric acid to KDG, which will not be sensed by CdaR. This shifts the dynamic range to higher concentrations.

Example Using Ligand Sequestration: B12 and btuB Aptamer Domain:

An aptamer is expressed within the cell to bind the sensed molecule and reduce its interaction with the sensor. The 5'-untranslated region (5'-UTR) of the *E. coli* btuB gene contains an aptamer that binds to vitamin B12 and its derivatives (Nahvi et al., Nucleic Acids Res. 32:143-150 (2004)). In the btuB riboswitch sensor selector strain, *E. coli* btuB 5'-UTR is placed 5' to the tetR regulator gene, controlling its translation; tetR in turn controls the selection gene (See FIG. 2). When a high level of the btuB vitamin B12 aptamer domain is transcribed in this strain, it binds to B12 within the cell, sequestering it so that there is a lower effective concentration to activate the btuB-tetR sensor. This shifts the dynamic range by increasing the concentration required by the sensor to achieve the same response.

Example VII

Toggled Selection for Library of MAGE Mutants (ToSLIMM)

MAGE (multiplex automated genome engineering) is a powerful tool for massively multiplexed engineering of pathway genes (Wang et al. Nature 460, 894-898 2009; Wang et al 2012 Nat Methods 9(6):591-3 (2012)). The method can generate a genomic library of over a billion variants in a day. The incidence of false positives may increase progressively with MAGE cycles. While a highly diversified population is important for finding the best producing strain, it also increases the likelihood of finding false positives. Accordingly, Toggled Selection Scheme for Library of MAGE Mutants (ToSLIMM) is provided as a method to reduce false positives resulting from MAGE.

Figure 11:
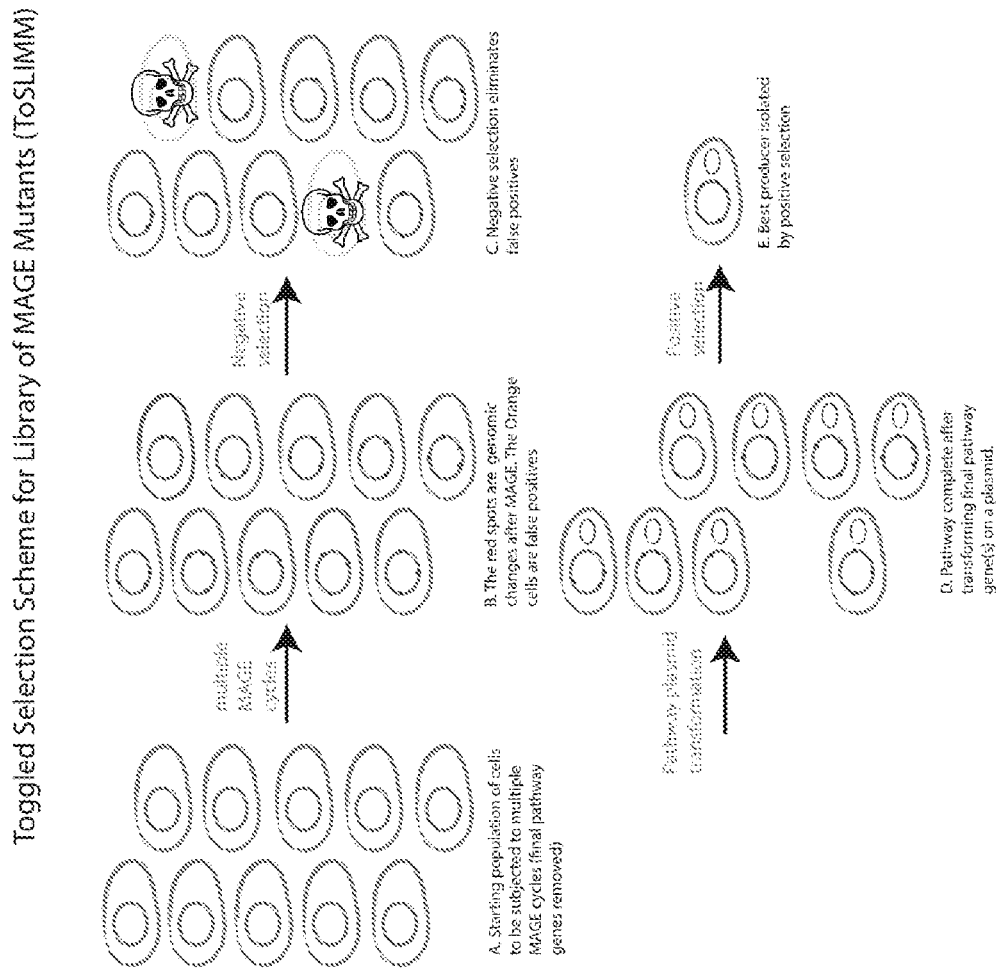
FIG. 11 is a schematic of the ToSLIMM protocol. The five panels describe the steps in the ToSLIMM protocol. (A) Starting population, last few pathway gene(s) removed. (B) Diversified population after MAGE. The red spots represent genomic changes. The orange cells are spontaneous mutants that result in false positives. (C) Negative selection eliminates false positives. (D) The pathway genes containing plasmid is introduced into the cells surviving negative selection. The pathway is now complete and metabolite is produced. (E) After positive selection, the best producer is isolated.

As shown in the schematic of FIG. 11, the method includes the steps of
1. Choose a positive-and-negative selectable marker (such as tolC) as the selector.
2. Put the last or last few genes of a pathway on a plasmid. This ensures that the pathway is incomplete and cannot produce the final product without these genes. Hence, the sensor-selector cannot be activated.
3. Perform multiple MAGE cycles on all remaining endogenous targets
4. Subject this diversified population to negative selection (colicin in the case of tolC). This step eliminates all the spontaneous mutants that are false positives. However, the non false positives are not killed because the plasmid containing pathway gene(s) required to complete the pathway is not present inside the cell. This step ensures that only the "true" false positives are eliminated.
5. Transform the plasmid into the surviving cells and select for cells containing the plasmid. Now the pathway is complete and all the cells in the diversified library can be interrogated for metabolite production.

6. Apply positive selection gradient on the transformed cells. Isolate cells that survive strong selection pressure

Example VIII

Naringen Production Pathway

Plasmid Construction for Heterologous Genes:

Two plasmids were constructed to express 4 heterologous genes for naringenin production. Plasmid 1 contains the p15A origin of replication, a carbenicillin resistance gene cassette, gene RgTALsyn controlled by a pTrc promoter and gene Pc4CLsyn controlled by a second pTrc promoter (Santos et al., Metabolic Engineering, 13:392-400 (2011)). Plasmid 2 contains a ColEI origin of replication, a kanamycin resistance gene cassette, gene PhCHS-A under control of a pLtetO promoter and gene MsCHI-1 under control of a second pLtetO promoter (Santos, et al., Metabolic Engineering, 13:392-400 (2011); Lutz and Bujard, Nucleic Acids Res. 1997 25(6):1203-10)). These plasmids were sequenced and naringenin and coumaric acid production were verified by liquid chromatography-mass spectrometry.

Genomic Diversification by MAGE Targeting Naringenin Production Genes:

Naringenin biosynthesis requires tyrosine and malonyl-CoA as inputs from cellular metabolism (Santos, et al., Metabolic Engineering, 13:392-400 (2011)). MAGE mutagenesis (Wang et al., Nature 460, 894-898 (2009)) of strain SSECttgR2 was used to create diversity in three pools, targeting genes shown to be involved in malonyl-CoA overproduction (Xu et al., Metabolic Engineering, 13:578-587 (2011)), genes shown to be involved in tyrosine overproduction (Eversloh et al., Appl. Genetics Mol. Biotechnol. 75:103-110 (2007)), or the conjunction. Genomic diversity targets for malonyl-CoA overproduction include the following: degenerate start codons 5'-BTG (fumB, fumC, mdh, acnA); premature stop codons (scpC, sucD); and degenerate ribosome binding sites 5'-DDRRRRRDDDD ending −3 bp relative to the start codon (accA, accB, accD, accD, aceE, aceF, lpd, gapA, pgk). Genomic diversity targets for tyrosine overproduction include the following: premature stop codons (tyrR, trpR); coding mutations shown to alleviate product inhibition (tyrA: M53I, A354V; aroG: D146N); and degenerate ribosome binding sites 5'-DDRRRRRDDDD ending −3 bp relative to the start codon (aroG, tyrA, pheA, aspC, tyrB, aroF, aroH, aroK, aroB, ydiB, aroD, aroE, aroL, aroC, aroA). The conjuction genomic target diversity includes all targets from both sets.

Selection Method for High Producer of Naringenin:

The ToSLIMM protocol was used to eliminate false positives and identify the best naringenin producer. The starting strain used for MAGE contains plasmid 1 (genes RgTALsyn and Pc4CLsyn), but no plasmid 2 (genes PhCHS-A and MsCHI-1). Therefore the final two steps of naringenin production remain incomplete. The starting strain is grown LB with carbenicillin resistance of plasmid 1 and diversified through six cycles of MAGE. After the sixth cycle, cells are grown in media containing LB with Carb and a gradient of colicin concentrations across a 96-well. Since, negative selection (with colicin) shouldn't affect the regular cells, the gradient is helpful in determining the maximum negative selection pressure that does not place a growth burden on the population. The population is then chosen from the highest colicin concentration with least burden and grown out in LB-carb medium. At mid-log, the cells are harvested, washed to make them electrocompetent and transformed with plasmid 2. After recovery, the transformed cells are grown in LB-Carb-Kan and IPTG overnight to enable production of naringenin.

Figure 12:
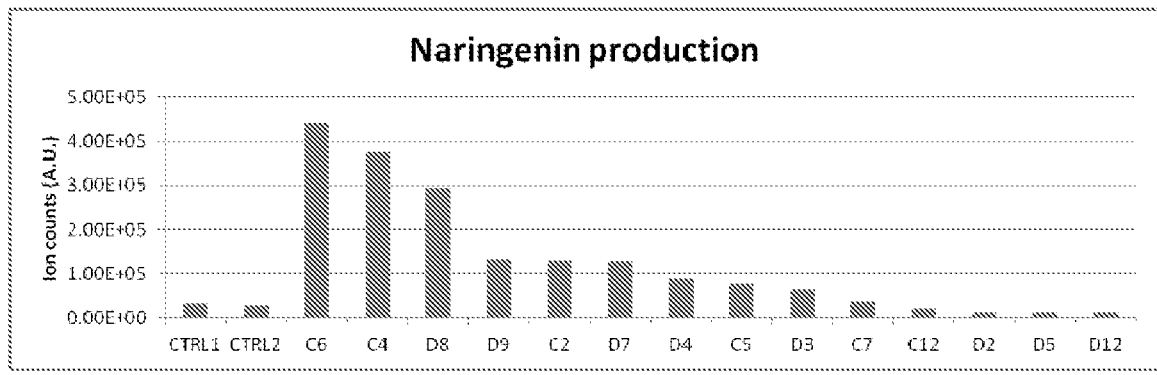
FIG. 12 is a graph of naringenin production levels for parent strain (CTRL1, CTRL2) and clones selected after MAGE (C6-D12). Production was measured using liquid chromatography-mass spectrometry and is reported as raw ion counts (arbitrary units). Highest production clone produces 12-fold more than parent strain.

Approximately 10^7 cells of overnight culture are added to each well of a 96-well plate where a gradient of positive selection pressure (with SDS) is applied. The cell density is monitored in a time course experiment over 24 hours. The cells that grow under strong selection pressure are isolated, regrown and assayed for naringenin production of LC-MS. FIG. 12 shows the result of the ToSLIMM protocol applied to naringenin pathway. The best producing strain has naringenin levels nearly 15 fold above the starting strain.

Example IX

Glucaric Acid Production Pathway

Plasmid Construction of Heterologous Genes:

A plasmid for glucaric acid biosynthesis was constructed from four PCR fragments by Gibson Assembly (Gibson et al., Nature Meth. 6(5):343-345 (2009)). The first fragment was amplified by PCR from pZE22 (Lutz and Bujard, Nucleic Acids Res. 1997 25(6):1203-10) and contained the ColE1 origin of replication and Kanamycin resistance marker. The second fragment was amplified by PCR from a Myo-inositol-oxygenase (MIOX) gene derived from Mus musculus and synthesized in an E. coli codon optimized form by Genscript. The forward primer was used to introduce a T7 promoter and RBS (FW primer: 5-TGCTAG-CAAGTAAGGCCGACTAATACGACTCACTATAGGGA-GAAAGAAGGAGGTAA CTCATAGTGAAAGTGGATGTTGGCCCGGA-3). The third fragment was amplified by PCR from the Saccharomyces cerevisiae genome and contained the gene inositol-1-phosphate synthase (INO1) (FW primer: 5-TAAGAAT-TCATTAAAGAGGAGAAAGAATTCATGACAGAAG ATAATATTGCTCCAATC ACC-3 RV primer: 5-ATGG-TACCTTTCTCCTCTTTAATGGTACCTTA-CAACAATCTCTCTTCGAATCTTAGTTC G-3). The fourth fragment was amplified by PCR from the genome of Agrobacterium tumefaciens and contained the gene uronate dehydrogenase (UDH). The plasmid was designated pT7GAEXP (Sequence 2).

Genomic Diversification by MAGE Targeting Glucaric Acid Production Genes:

MAGE (Wang et al. Nature 460, 894-898 (2009)) was used to change the SSECcdaR genome in seven locations. The genes garK and uxaC were each targeted for complete knockout by the introduction of two premature stop codons. The genes suhB, pgi, sthA, zef and mdh were modified at their ribosomal binding sites (RBS). Degenerate oligomers were used to introduce semi-random RBS at each gene in order to span a complete range of expression levels. Each cell in the diversified population may contain zero to seven genomic modifications. Two loci have two possibilities (premature stop codons or unchanged) while five loci have $1.8 \times 10^5$ possible ribosomal binding sites. The theoretical library size after MAGE would be $7.0 \times 10^{26}$, however practicality limits this to roughly one billion. The oligomers used are listed as Sequence 3 [Appended]. Five cycles of MAGE were completed. The resulting collection of strains was designated SSECcdaR-D.

Diversification of Glucaric Acid Production Plasmid:

MIOX was amplified by PCR from the pT7GAEXP plasmid using a single forward primer (5-ATGAAAGTG-GATGTTGGCCCGGAC-3) and a mixture of degenerate reverse primers (5-CTTTAACGGAGGTGATTGGAG-CAATATTATCTTCTGTCATGAATTCTTYYBYYYYTTT AATGAATTCTTACCACGACAGGGTGCCCGGAC-3). INO1 was amplified by PCR from the pT7GAEXP plasmid (Forward primer: 5-AAGAATTCATGACAGAAGATAAT-ATTGCTCCAATC-3 Reverse primer: 5-TTTAATGGTAC-CTTACAACAATCTCTCTTCGAATC-3). The PCR products of MIOX and INO1 were assembled by overlap extension PCR (citation) to create a single construct with a single degenerate RBS preceding the INO1 gene. The MIOX-(semi-random-RBS)-INO1 construct was amplified by PCR with two degenerate primers that also contained Bsa1 restriction sites (Forward primer: 5-AACGAACCA-GAACCTGCAGGAATTCCACACCAGGTCT-CAAGAATTCATTAAARRRRV RRAAGGTACCAT-GAAAGTGGATGTTGG-3 Reverse primer: 5-GCGGTTGTTGAAGGTATCCGTAAACCACACCAG-GTCTCAGGTACTTTYYBYYYYTTTA ATGGTACCT-TACAACAATCTCTCTTCG-3) to create a PCR product that contained three locations with degenerate bases. This PCR product was again amplified by PCR with primers annealing at the extreme ends of the template (Forward primer: 5-AACGAACCAGAACCTGCAGGAATTC-3 Reverse primer: 5-GCGGTTGTTGAAGGTATCCG-TAAAC-3). The backbone and UDH gene were amplified by PCR from pT7GAEXP with primers that contained Bsa1 restriction sites (Forward primer: CACACCAGGTCTCAT-ACCATGAAACGGCTTCTTGTTAC Reverse primer: CACACCAGGTCTCATTCTCTCCCTATAGTGAGTCGT-ATTAGTCG). Both the degenerate insert and the vector were digested with Bsa1 restriction enzyme (New England Biolabs) and ligated with T4 DNA ligase (New England Biolabs). The resulting plasmid had a theoretical library size of 7 million and was designated pT7GAEXP-degen.

Figure 13:
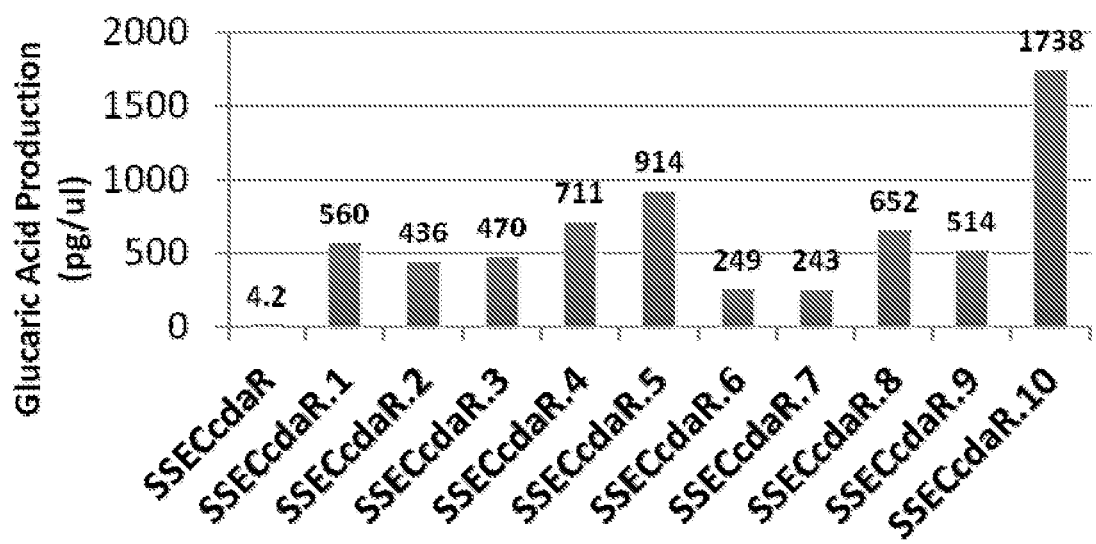
FIG. 13 is a graph of glucaric acid production levels for parent strain (SSECcdaR) and clones after MAGE mutagenesis and selection (SSECcdaR.1-10). Production level for the highest clone is 415-fold higher than the parent strain.

Selection of High Producer of Glucaric Acid from Genomic Library:

The ToSLIMM protocol was used to eliminate false positives and identify the best glucaric acid producer. The collection of strains SSECcdaR-D was grown overnight to saturation. The saturated culture was inoculated to 3 ml fresh LB at a dilution of 1:100. Colicin was added at a ratio of 1:10. The culture was grown at 30° C. for 48 hours. This culture was then diluted 1:100 into 3 ml fresh LB and grown to an OD 0.5. The cells were harvested by centrifugation and washed twice with deionized water at 4° C. 100 ng of plasmid pT7GAEXP was electroporated into SSECcdaR-D. The cells were then grown for 1 hour in outgrowth media before being diluted 20 fold into LB supplemented with 50 ug/ml kanamycin. The cells were grown to saturation overnight. The cells were back-diluted 1:100 in LB supplemented with 50 ug/ml kanamycin, 10 mM glucose and 1 mM IPTG. After 24 hours this culture was used to inoculate 48 micro-titer wells at a 1:100 dilution. Each well contained LB supplemented with 10 mM glucose, 1 mM IPTG, 50 ug/ml kanamycin and 0.005% SDS. The correct SDS concentration was determined from a previous experiment characterizing the sensor response to glucaric acid. The selection plate was then monitored for absorbance at 600 nm while incubating with shaking at 30° C. Wells that showed growth were used to inoculate non-selective cultures for further analysis. FIG. 13 shows the results of ToSLIMM protocol applied to the glucaric acid pathway. The best producing strains produced glucaric acid on average 415 fold above the parent strain.

Selection of High Producer from Plasmid Library:

SSECcdaR was grown to saturation and harvested by centrifugation. The cell pellet was washed twice with deionized water and electroporated with 100 ng of the library of diversified plasmids pT7GAEXP-degen. The cells were then grown for 1 hour in outgrowth media before being diluted 20 fold into LB supplemented with 50 ug/ml kanamycin. The cells were grown to saturation overnight. The cells were back-diluted 1:100 in LB supplemented with 50 ug/ml kanamycin, 10 mM glucose and 1 mM IPTG. After 24 hours the culture was used to inoculate 96 micro-titer wells at a 1:100 dilution. Each well contained LB supplemented with 1 mM IPTG, 50 ug/ml kanamycin and 0.005% SDS. The amount of glucose was varied between 50 mM and 3 mM in order to challenge the cells with differing selective pressures. The selection plate was then monitored for absorbance at 600 nm while incubating with shaking at 30° C. Wells that showed growth were used to inoculate non-selective cultures for further analysis.

The contents of all references, patents and published patent applications cited throughout this application are hereby incorporated by reference in their entirety for all purposes.

EQUIVALENTS

Other embodiments will be evident to those of skill in the art. It should be understood that the foregoing description is provided for clarity only and is merely exemplary. The spirit and scope of the present invention are not limited to the above example, but are encompassed by the claims. All publications, patents and patent applications cited above are incorporated by reference herein in their entirety for all purposes to the same extent as if each individual publication or patent application were specifically indicated to be so incorporated by reference.

What is claimed is:

1. A method of selecting a subset of microbes for the production of a metabolite comprising
    placing a population of microbes in an environment of a toxin, wherein the toxin is external to the population of microbes,
    wherein the population of microbes has been genetically modified to include exogenous DNA encoding for an antidote gene to the toxin,
    wherein the population of microbes has been genetically modified to include exogenous DNA encoding a sensor biomolecule which when expressed regulates expression of the antidote gene by the microbes through a cognate nucleic acid sequence located 5' to the DNA encoding the antidote gene, wherein the sensor biomolecule is a transcription factor, riboswitch, two-component signaling protein or a nuclear hormone receptor,
    wherein the population of microbes has been genetically modified to include exogenous DNA encoding genes to produce a metabolite binding partner of the sensor, which when produced binds to the sensor to induce expression of the antidote gene in a manner dependent on the concentration of the produced metabolite, and
    selecting a subset of microbes that produce sufficient metabolite to prevent microbe death,
    wherein the sensor biomolecule and its corresponding metabolite binding partner is selected from the group consisting of cdaR and glucaric acid, ttgR and naringennin, btuB riboswitch and cobalamin, mphR and macrolides, benM and muconic acid, alkS and medium chain n-alkanes, xylR and xylose, araC and arabinose, gntR and Gluconate, galS and galactose, trpR and tryptophan, qacR and berberine, rmrR and Phytoalexin, cymR and cumate, melR and melibiose, rafR and raffinose, nahR and salicylate, nocR and nopaline, clcR and Chlorobenzoate, varR and virginiamycin, rhaR and rhamnose, PhoR and phosphate, MalK and malate, GlnK and glutamine, retinoic acid receptor and retinoic acid, estrogen receptor and estrogen, and ecdysone receptor and ecdysone, wherein the toxin and antidote pair is selected from the group consisting of SDS:tolC, colicin:tolC (negative selection), kanamycin:kanamycin nucleotidyltransferase, chloramphenicol:chloramphenicol acyl transferase, ampicillin:beta lactamase, tetracycline:tetracycline efflux pump tetA, nickel chloride:tetracycline efflux pump tetA (negative selection), and 5-fluoroorotic acid:URA3 (negative selection).

2. The method of claim 1 further comprising
genetically modifying the subset of microbes to alter genes that affect production of the metabolite directly or indirectly,
subjecting the subset of microbes to a subsequent environment of the toxin having a concentration greater than the previous environment,
and selecting a subsequent subset of microbes the produce sufficient metabolite to prevent microbe death.

3. The method of claim 2 further comprising
repeating in sequence: (1) genetically modifying the subsequent subset of microbes by altering genes that affect the production of the metabolite, (2) subjecting the genetically altered microbes to a subsequent environment of a toxin having a concentration greater than a previous environment, and (3) selecting a further subsequent subset of microbes that produce sufficient metabolite to prevent microbe death, said repeating step resulting in optimized metabolite producing microbes.

4. The method of claim 1 wherein binding of the metabolite to the sensor regulates gene expression to induce production of the antidote gene in a manner dependent on the concentration of the expressed metabolite.

5. The method of claim 4 wherein a positive selection marker is used to select the subset of microbes that produce sufficient metabolite to prevent microbe death.

6. The method of claim 4 wherein the sensor regulates the expression of two or more antidote genes independently and two or more toxins are used to select the subset of microbes that produce sufficient metabolite to prevent microbe death.

7. The method of claim 1 wherein binding of the metabolite to the sensor regulates gene expression to induce production of the antidote gene in a manner dependent on the concentration of the expressed metabolite.

8. The method of claim 7 wherein a negative selection marker is used to eliminate false positives that detoxify the microbe despite not producing sufficient metabolite.

9. The method of claim 1 wherein the population of microbes have been genetically modified to include two or more redundant copies of the exogenous DNA encoding the sensor in order to reduce false positives.

10. The method of claim 1 wherein the sensor also regulates its own expression through a cognate nucleic acid sequence located 5' to the DNA sequence encoding the sensor in order to reduce false positives.

11. The method of claim 1 wherein the degradation rate of the antidote gene is increased by encoding a degradation signal within the antidote gene in order to reduce false positives.

12. The method of claim 2 wherein the step of genetically modifying the subset of microbes to alter genes that produce the metabolite includes multiplexed automated genome engineering.

13. The method of claim 2 wherein the step of genetically modifying the subset of microbes includes making a plasmid library of pathway genes.

14. The method of claim 2 wherein the step of genetically modifying the subset of microbes includes making a plasmid library of genomic fragments of any organism.

15. The method of claim 2 wherein the step of genetically modifying the subset of microbes includes making a plasmid library of metagenomic sequences.

16. The method of claim 12 wherein the multiplexed automated genome engineering includes reducing spontaneous background mutants.

17. The method of claim 12 wherein the multiplexed automated genome engineering includes reducing spontaneous background mutants by pretreatment with a negative selector.

18. The method of claim 1 wherein concentration of the metabolite exposed to the sensor is attenuated.

19. The method of claim 18 wherein the concentration of the metabolite exposed to the sensor is attenuated by expressing one or more proteins to export the metabolite outside of the cell.

20. The method of claim 18 wherein the concentration of the metabolite exposed to the sensor is attenuated by expressing one or more enzymes that convert the metabolite to another metabolite having less interaction with the sensor.

21. The method of claim 18 wherein the concentration of the metabolite exposed to the sensor is attenuated by expressing a biomolecule that binds to the metabolite and reduces its interaction with the sensor.

* * * * *